(12) United States Patent
Yakovenko et al.

(10) Patent No.: US 9,839,200 B2
(45) Date of Patent: Dec. 12, 2017

(54) WALKWAY DEVICE AND METHOD FOR QUANTITATIVE ANALYSIS OF GAIT AND ITS MODIFICATION IN RODENTS

(71) Applicant: West Virginia University, Morgantown, WV (US)

(72) Inventors: Sergiy Yakovenko, Morgantown, WV (US); Matthew Boots, Morgantown, WV (US); Ryan Ellison, Washington, WV (US); Kiril Tuntevski, Morgantown, WV (US)

(73) Assignee: West Virginia University, Morgantown, WV (US)

( * ) Notice: Subject to any disclaimer, the term of this patent is extended or adjusted under 35 U.S.C. 154(b) by 0 days.

(21) Appl. No.: 15/259,216

(22) Filed: Sep. 8, 2016

(65) Prior Publication Data

US 2017/0064929 A1 Mar. 9, 2017

Related U.S. Application Data

(60) Provisional application No. 62/215,977, filed on Sep. 9, 2015.

(51) Int. Cl.
*A01K 29/00* (2006.01)
*A01K 1/03* (2006.01)
(Continued)

(52) U.S. Cl.
CPC ............ *A01K 29/005* (2013.01); *A01K 1/031* (2013.01); *A01K 15/027* (2013.01); *A61B 5/1038* (2013.01); *A61B 5/112* (2013.01)

(58) Field of Classification Search
CPC ............ A63B 2220/40; A63B 2220/53; A63B 2220/13; A63B 2220/16; A63B 2220/803;
(Continued)

(56) References Cited

U.S. PATENT DOCUMENTS 4,774,679 A * 9/1988 Carlin .................. A61B 5/0002
273/454
4,935,887 A * 6/1990 Abdalah ................ A63B 24/00
702/141
(Continued)

FOREIGN PATENT DOCUMENTS

WO WO 2013179230 A1 * 12/2013 ......... A61N 1/36003

OTHER PUBLICATIONS

Basso, D.M. et al., A Sensitive and Reliable Locomotor Rating Scale for Open Field Testing in Rats, Journal of Neurotrauma, 1995, 1-21, vol. 12, No. 1, Mary Ann Liebert, Inc.
(Continued)

*Primary Examiner* — Yvonne Abbott-Lewis
(74) *Attorney, Agent, or Firm* — Buchanan Ingersoll & Rooney PC; Craig G. Cochenour, Esq.

(57) ABSTRACT

A system and method for quantitatively assessing the changes in control of asymmetric locomotor behavior of an animal comprising analyzing the phase modulation in response to imposed asymmetric stepping tasks for quantitatively assessing changes in control of asymmetric locomotor behavior. A walkway gait device is provided comprising an elevated grid having at least one platform having a face and at least two or more pegs located in front or back of said platform, wherein each peg has a pressure sensor or switch in communication with a detection unit for capturing the pressure detected by one or more of the pressure sensors or switches. Preferably, the grid of the walkway gait device has at least three platforms to form a closed path loop.

37 Claims, 12 Drawing Sheets

(51) Int. Cl.
*A01K 15/02* (2006.01)
*A61B 5/11* (2006.01)
*A61B 5/103* (2006.01)

(58) Field of Classification Search
CPC ... A61B 2562/0219; A61B 5/11; A61B 5/112;
A01K 29/00; A01K 29/005; A01K 1/031;
A01K 15/027
USPC ...... 119/421, 908; 702/141; 73/172, 379.01,
73/862, 53, 865.4, 379.04, 488, 862.27,
73/862.59
See application file for complete search history.

(56) References Cited

U.S. PATENT DOCUMENTS

| | | | | |
|---|---|---|---|---|
| 4,972,177 | A * | 11/1990 | Nolan | G08B 21/0446 200/DIG. 2 |
| 5,138,550 | A * | 8/1992 | Abraham | A63K 3/00 119/702 |
| 5,485,402 | A * | 1/1996 | Smith | A61B 5/1038 340/870.01 |
| 5,736,656 | A * | 4/1998 | Fullen | G01L 1/205 73/172 |
| 6,266,623 | B1 * | 7/2001 | Vock | A42B 3/0433 702/41 |
| 6,347,603 | B1 * | 2/2002 | Felger | A01K 15/027 119/700 |
| 6,532,901 | B2 * | 3/2003 | Isley | A01K 29/005 119/174 |
| 6,536,377 | B2 * | 3/2003 | Beaver | A01K 13/00 119/174 |
| 6,611,789 | B1 * | 8/2003 | Darley | A61B 5/1038 702/141 |
| 8,704,668 | B1 * | 4/2014 | Darrell | A01K 29/005 340/500 |
| 8,773,269 | B2 * | 7/2014 | Richardson | A61B 5/0002 340/539.11 |
| 2002/0010056 | A1 * | 1/2002 | Borsheim | A61H 3/00 482/66 |
| 2002/0115945 | A1 * | 8/2002 | Herman | A61H 3/00 601/15 |
| 2002/0157617 | A1 * | 10/2002 | Reinkensmeyer | A01K 15/027 119/728 |
| 2003/0064869 | A1 * | 4/2003 | Reinkensmeyer | A61B 5/1038 482/100 |
| 2003/0114894 | A1 * | 6/2003 | Dar | A61N 1/0452 607/48 |
| 2003/0196607 | A1 * | 10/2003 | Hong | A01K 29/005 119/421 |
| 2012/0180731 | A1 * | 7/2012 | Garner | A01K 29/005 119/417 |
| 2012/0330391 | A1 * | 12/2012 | Bradley | A61N 1/0551 607/117 |
| 2016/0270364 | A1 * | 9/2016 | Woolf | A01K 1/031 |
| 2016/0279418 | A1 * | 9/2016 | Courtine | A61N 1/0551 |
| 2016/0346156 | A1 * | 12/2016 | Walsh | A63B 21/4009 |

OTHER PUBLICATIONS

Curzon, P. et al., Chapter 8 The Behavioral Assessment of Sensorimotor Processes in the Mouse: Acoustic Startle, Sensory Gating, Locomotor Activity, Rotarod, and Beam Walking, NCBI Bookshelf, A Service of the National Library of Medicine, National Institutes of Health, 2009, 1-37, CRC Press.
Basso, D.M. et al., Graded Histological and Locomotor Outcomes after Spinal Cord Contusion Using the NYU Weight-Drop Device versus Transection, Experimental Neurology, 1996, 244-258, vol. 139, Academic Press, Inc.
Li, S. et al., Assessing gait impairment after permanent middle cerebral artery occlusion in rats using an automated computer-aided control system, Behavioural Brain Research, 2013, 174-191, vol. 250, Elsevier B.V.
Vandeputte, C. et al., Automated quantitative gait analysis in animal models of movement disorders, BMC Neuroscience, 2010, 1-11, BioMed Central.
Yakovenko, S. et al., A hierarchiacal perspective on rhythm generation of locomotor control, Progress in Brain Research, 2011, 151-166, vol. 188, Elsevier B.V.
Giszter, S.F. et al., How spinalized rats can walk: biomechanics, cortex, and hindlimb muscle scaling-implictions for rehabilitation, Annals of the New York Academy of Sciences, 2010, 279-293, vol. 1198, New York Academy of Sciences.
Smith, J.L. et al., The Chronic Spinalized Cat: A Model for Neuromuscular Plasticity, Birth Defects: Original Article Series, 1983, 357-373, vol. 19, No. 4, March of Dimes Birth Defects Foundation.
Yakovenko, S. et al., A Motor Cortical Contribution to the Anticipatory Postural Adjustments That Precede Reaching in the Cat, J. Neurophysiol, 2009, 853-874, vol. 102, The American Physiological Society.
Yakovenko, S. et al., Sequential Activation of Motor Cortical Neurons Contributes to Intralimb Coordination During Reaching in the Cat by Modulating Muscle Synergies, J. Neurophysiol, 2011, 388-409, vol. 105, The American Physiological Society.
Pizzi, A. et al., Gait in Hemiplegia: Evaluation of Clinical Features with the Wisconsin Gait Scale; J. Rehabil Med. 2007, 170-174, vol. 39, Foundation of Rehabilitation Information.
Bohannon, R.W., et al., Importance of four variables of walking to patients with stroke, International Journal of Rehabilitation Research, 1991, 246-250, vol. 14, Chapman & Hall.
Richards, C., et al., Chapter 25: Gait Velocity as an Outcome Measure of Locomotor Recovery After Stroke, Gait Analysis, Theory and Applications, 1995, 355-364.
Thaut, M.H., et al., Rhythmic facilitation of gait training in hemiparetic stroke rehabilitation, Journal of the Neurological Sciences, 1997, 207-212, vol. 151, Elsevier Science B.V.
Hsu, A-L., et al., Analysis of Impairments Influencing Gait Velocity and Asymmetry of Hemiplegic Patients After Mild to Moderate Stroke, Arch Phys Med. Rehabil, 2003, 1185-1193.
Jansen, K., et al., Muscle contributions to center of mass acceleration adapt to asymmetric walking in healthy subjects, Gait & Posture, 2013, 739-744, vol. 38, Elsevier B.V.
Halbertsma, J.M., The Stride Cycle of the Cat: The Modelling of Locomotion By Computerized Analysis of Automatic Recordings, Acta Physiol Scand, Suppl., 1983, 4-75, vol. 521, Delft & Stockholm.
Metz, G. A. et al., The Ladder Rung Walking Task: A Scoring System and its Practical Application, Journal of Visualized Experiments, 2009, 1-4.
Brown, T.G. et al., The Intrinsic Factors in the Act of Progression in the Mammal, 1911, 308-319, Royal Society Publishing.
Kiehn, O., Locomotor Circuits in the Mammalian Spinal Cord, Annu. Rev. Neurosci., 2006, 279-306, vol. 29, Annual Reviews.
Blitz, D.M. et al., State-Dependent Presynaptic Inhibition Regulates Central pattern Generator Feedback to Descending Inputs, The Journal of Neuroscience, 2008, 9564-9574, vol. 28, No. 38, Society for Neuroscience.
Martin, J.H. et al., Red nucleus and motor cortex: parallel motor systems for the initiation and control of skilled movement, Behavioural Brain Research, 1988, 217-223, vol. 28, Elsevier Science Publishers B.V.
Drew, T. et al., Role of the motor cortex in the control of visually triggered gait modifications, Can. J. Physiol, Pharmacol., 1996, 426-442, vol. 74, NRC Canada.
Drew, T. et al., Cortical mechanisms involved in visuomotor coordination during precision walking, Brain Research Reviews, 2008, 199-211, vol. 57, Elsevier B.V.
Longa, E.Z. et al., Reversible Middle Cerebral Artery Occlusion Without Craniectomy in Rats, Stroke, 1989, 84-91, vol. 20, No. 1, American Heart Association, Inc.
Uluc, K. et al., Focal Cerebral Ischemia Model by Endovascular Suture Occlusion of the Middle Cerebral Artery in the Rat, Journal of Visualized Experiments, 2011, 1-5, Creative Commons.

(56) References Cited

OTHER PUBLICATIONS

Hackney, D.B. et al., Postmortem Magnetic resonance Imaging of Experimental Spinal Cord Injury: Megnetic Resonance Findings versus in Vivo Functional Deficit, Neurosurgery, 1994, 1-16, vol. 35, No. 6, Congress of Neurological Surgeons.

Kjaerulff, O. et al., Distribution of Networks Generating and Coordinating Locomotor Activity in the Neonatal Rat Spinal Cord in Vitro: A Lesion Study, The Journal of Neuroscience, 1996, 5777-5794, vol. 16, No. 18, Society for Neuroscience.

Liddell, E.G.T. et al., Striatal and Pyramidal Lesions in the Cat, Brain, 264-279, vol. LXIX.

Beloozerova, I.N. et al., The Role of the Motor Cortex in the Control of Accuracy of Locomotor Movements in the Cat, Journal of Physiology, 1993, 1-25, vol. 461.

Hill, K.D. et al., Retest Reliability of the Temporal and Distance Characteristics of Hemiplegic Gait Using a Footswitch System, Arch Phys Med Rehabil, 1994, 577-583, vol. 75.

Hillyer, J.E. et al., A New Measure of Hindlimb Stepping Ability in Neonatally Spinalized Rats, Behavioural Brain Research, 2009, 291-302, vol. 202, Elsevier B.V.

\* cited by examiner

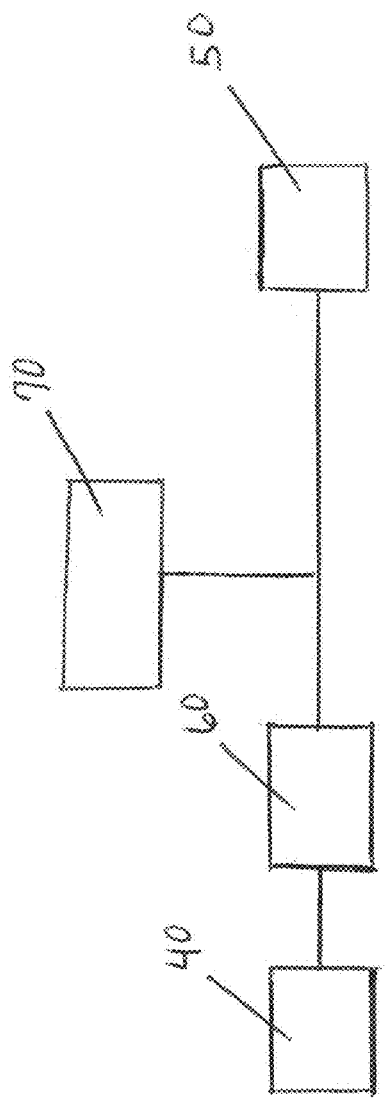

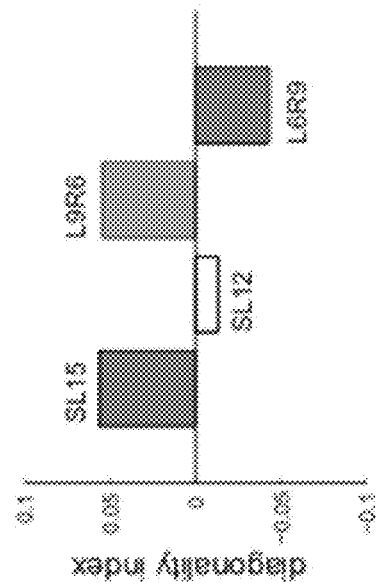

WALKWAY DEVICE AND METHOD FOR QUANTITATIVE ANALYSIS OF GAIT AND ITS MODIFICATION IN RODENTS

CROSS-REFERENCE TO RELATED APPLICATIONS

This utility patent application claims the benefit of U.S. Provisional Patent Application Ser. No. 62/215,977, filed Sep. 9, 2015. The entire contents of U.S. Patent Application Ser. No. 62/215,977 is incorporated by reference into this utility patent application as if fully written herein.

STATEMENT REGARDING FEDERALLY SPONSORED RESEARCH

This invention was made with government support under grant number U54GM104942 awarded by the National Institute of Health/NIGMS, and grant number P20GM109098 (CoBRE) awarded by the National Institute of Health. The government has certain rights in this invention.

FIELD OF THE INVENTION

Embodiments disclosed herein relate to devices and methods for quantitative analysis of gait, and in particular devices and methods that are able to impose and measure symmetric and asymmetric gaits with stride lengths that span the range from preferred to critical unstable lengths.

BACKGROUND OF THE INVENTION

Typical gait analysis devices and methods can provide overall evaluation of motor impairment due to disease or trauma. An example of an existing system can be obtained from Noldus (http://www.noldus.com/CatWalk-XT/) for $48,170, which may include analysis software and a device. The Noldus CatWalk™ XT may be based on the Ladder Run Walking test or task, which can include: 1) footprint outline (print area, stand index, intensity); 2) distances between footprints (base of support, stride length); and, 3) time relationships between footprints (cadence, support and swing duration). The device may automatically detect the timing of gait phases in self-paced locomotion. Noldus CatWalk™ XT software may further provide qualitative and quantitative analysis of individual footfall parameters. Yet, one deficiency exhibited by this and similar systems is the lack of capability to instruct animals about a desired pattern of locomotion.

The Ladder Rung Walking task/test had been developed for mice (Farr: 2006) and for rats (Metz:2009) to test the control of paw placement that had been impaired after suffering damage to the corticospinal pathways. The task/test tends to rely on methods to impose bilateral pattern of locomotion without any means to control which limb is used to step on rungs. For reasons explained below, this can lead to deficiencies in existing gait analysis devices and methods.

Behavioral assays can be used for assessing sensorimotor impairment in the central nervous system (CNS). One of the more sophisticated methods for quantifying locomotor deficits in rodents can be to measure minute disturbances of unconstrained gait overground (e.g. manual the Basso, Beattie, and Bresnahan (BBB) locomotor scale or automated CatWalk). However, cortical inputs are not required for generation of basic locomotion produced by the spinal central pattern generator (CPG). Thus, unconstrained walking tasks, such as those relied upon by existing gait devices and methods, only indirectly test for locomotor deficits caused by motor cortical impairment.

Post-stroke morbidity in a surviving population may include gross motor impairments that can pose a challenge for quantitative evaluation in both post-stroke humans and animal models of neurologic impairment.[1] For example, in a clinical setting, these motor impairments are typically measured using subjective criteria, which tend to be more sensitive to severe impairment rather than moderate impairment. Yet, a majority of surviving patients exhibit moderate impairment as opposed to severe impairment. In addition, assessments of post-injury motor behavior in animals commonly use subjective assessment techniques (e.g. BBB locomotor scale method) to generate the subjective criteria alluded to above.[2,3] While these subjective evaluation methods may assist with translation between gait rehabilitation studies in quadruped animal models and humans, such methods may not be as effective for assessing details of motor deficits associated with activity of separate muscle groups. This is compounded with the fact that the assessment of motor cortical contribution to locomotion (the putative culprit of motor deficit in cerebrovascular accident) may only be obtained indirectly when using such techniques, even when employing advanced automated quantitative methods.[4,5] Again, this can be due to such techniques' heavy reliance on open-field or linear walking tasks.

Open-field or linear walking tasks may not require cortical contribution, and thus can be performed by the neural mechanisms of the spinal cord, i.e. the CPG network. Yet, the CPG network is typically spared in most animal models of neural damage, e.g. spinalized animals[6-8]. This is in spite of the fact that essential cortical contribution to these spinal mechanisms had been experimentally implicated in tasks that require anticipated postural adjustments[9] and reaching[10], as well as precise stepping[10].

Moreover, most neurological damage is asymmetric. For example, stroke generally causes hemiparesis, e.g. weakness on one side of the body, which can result in an asymmetric gait.[11-14] The asymmetry of hemiplegic gait can be produced by asymmetric spatiotemporal muscle activation most significantly manifested in the shortening of the extensor-associated stance phase and the lengthening of the flexor-associated swing phase of the step cycle on the paretic side.[15,16] This trend has not yet been explored across a range of locomotor speeds in healthy or paretic animals.

The present invention is directed toward overcoming one or more of the above-identified problems.

SUMMARY OF THE INVENTION

Spinal cord injuries and/or stroke often produce asymmetric motor disabilities that reduce biomechanical efficiency. Rodents can be de facto models for the biomedical research of neural trauma, and systems and methods using rodents have been developed to assess biomechanical efficiency. Yet, artisans have failed to provide systems and methods that can effectively analyze the details of sensorimotor control from rodent behavioral performance. Prior to the date of this invention, no commercial device or method is available that is able to impose symmetric and asymmetric gaits with stride lengths that span the range from preferred to critical unstable lengths. Moreover, no existing device or method has been able to provide an easy-to-learn task that can challenge either stereotypical pathways of the spinal cord and/or the descending neural pathways responsible for the precise limb placement.

In one embodiment of this invention, a walkway device including a frame having pegs with a sensor array is provided. In another embodiment, a method can include a training paradigm is provided. In some embodiments, the sensor is a 3D printable sensor enclosure. In at least one embodiment of this invention, a device to modify systematically gait parameters and to evaluate locomotor performance in animals, for example, in rodents, is provided. Other devices for gait analysis in rodents do not have means to impose step restrictions for testing rehabilitation interventions after injury or basic research. Yet, the inventive device and method can impose desired stride length, inter-limb phase, and an incline of locomotor path. In addition, the duration of locomotor phases can be automatically measured and logged for further the assessment of impairment or function.

As used herein, the term animal refers to any member of the animal kingdom, including for example, but not limited to rodents and *Homo sapiens*.

In an exemplary embodiment, a method for quantitatively assessing the changes in control of asymmetric locomotor behavior of an animal can include analyzing the phase modulation in response to imposed asymmetric stepping tasks as set forth in this application for quantitatively assessing changes in control of asymmetric locomotor behavior. The method can further include observing changes in whole body coordination of said animal requiring diagonal coupling between contralateral forelimbs and hind-limbs of said animal characterized by differences in diagonal angle. The method can further include providing an animal having either a focal stroke or spinal cord hemilesion.

In an exemplary embodiment, a walkway gait device can include an elevated grid (framework) having at least one platform having a face and at least two or more pegs located in front or back of said platform, each peg having a face and at least one side that extends vertically from said face, said face of said peg positioned in proximity to said face of said platform, including wherein each peg has a pressure sensor or switch, wherein one or more of said pressure sensors or switches are in communication with a detection unit for capturing the pressure detected by one or more of said pressure sensors or switches. In some embodiments, one or more said pegs can be adjusted in one or more of a horizontal, a lateral, or a vertical direction relative to said face of said platform. In some embodiments, said platform and at least two pegs can be located in succession of each other relative to said platform, and a second platform located in juxtaposition to a peg that can be located farthest from said platform such that the pegs are located and spaced between said platform and said second platform. In some embodiments, one or more said pegs may be adjusted in one or more of a horizontal, a lateral, or a vertical direction relative to said face of said platform and said face of said second platform. In some embodiments, said grid can contain at least three platforms each having its own face and wherein each platform is separated from each other by at least two of said pegs, such that said three or more platforms form a closed loop path. In some embodiments, one or more said pegs may be adjusted in one or more of a horizontal, a lateral, or a vertical direction relative to said face of said platform. In some embodiments, the face of at least one of said pegs may be tilted up or down relative to the face of another peg or the face of at least one or more of said platforms.

Another exemplary embodiment can include any of the methods or walkway gait devices as set forth in the attached specification.

In another exemplary embodiment, a device for quantitative analysis of gait can include a support framework structured to support a plurality of pegs, the plurality of pegs forming a walkway to accommodate an animal walking along the plurality of pegs, the walkway comprising a first distal end and a second distal end. The device can further include a rest platform located at each of the first distal end and the second distal end. The device can further include at least one sidewall affixed to the support framework adjacent the walkway. The device can further include a path defined by the walkway and the at least one sidewall, the path comprising a central pathway running along its center from the first distal end to the second distal end forming a path first side and a path second side. The device can further include at least one sensor and at least one detection unit associated with at least one peg, the at least one sensor generating a signal when a foot by the animal is placed on the at least one peg and transmitting the signal to the detection unit, the detection unit detecting placement of the foot by the animal on the at least one peg. In some embodiments, each peg can include a platform section upon which the animal places the foot when walking along the path. In some embodiments, the plurality of pegs can be arranged in a linear array along the path and each peg may be arranged in a staggered manner so that the platform section of each adjacent peg in the linear array may be located on an opposite side of the central pathway. In some embodiments, a distance between each adjacent platform section can be (d) and a distance between each consecutive platform section of a same side of the central pathway can be a stride-length (SL). In some embodiments, placement of each peg relative to other pegs and relative to the support framework can be adjustable.

In another exemplary embodiment, a device for quantitative analysis of gait can include a support framework configured as a square structure to support a plurality of pegs, the support framework comprising a first side-length, a second side-length, a third side-length, and a fourth side-length, the plurality of pegs forming a walkway along each side-length to accommodate an animal walking along the plurality of pegs, each walkway comprising a distal end located at each corner of the support framework. The device can further include a rest platform located at each corner. The device can further include at least one sidewall affixed to the support framework adjacent each walkway. The device can further include a path defined by each walkway and the at least one sidewall adjacent thereto, the path comprising a central pathway running along its center from the distal ends of each walkway forming a path first side and a path second side. The device can further include at least one sensor and at least one detection unit associated with at least one peg within each walkway, the at least one sensor generating a signal when a foot by the animal is placed on the at least one peg and transmitting the signal to the detection unit, the detection unit detecting placement of the foot by the animal on the at least one peg. In some embodiments, each peg can include a platform section upon which the animal places the foot when walking along the path. In some embodiments, the plurality of pegs can be arranged in a linear array along the path and each peg can be arranged in a staggered manner so that the platform section of each adjacent peg in the linear array may be located on an opposite side of the central pathway. In some embodiments, a distance between each adjacent platform section can be (d) and a distance between each consecutive platform section of a same side of the central pathway can be a stride-length (SL). In some embodiments, placement of each peg relative to other pegs and relative to the support framework can be. In some embodiments, the (d) and the (SL) on an individual path are at least two parameters that can define a condition.

In some embodiments, the condition for the path of the first side-length can be different from the condition for the path of the second side-length, the condition for the path of the third side-length, and the condition for the path of the fourth side-length. In some embodiments, the condition for the path of the second side-length can be different from the condition for the path of the first side-length, the condition for the path of the third side-length, and the condition for the path of the fourth side-length. In some embodiments, the condition for the path of the third side-length can be different from the condition for the path of the first side-length, the condition for the path of the second side-length, and the condition for the path of the fourth side-length. In some embodiments, the condition for the path of the fourth side-length can be different from the condition for the path of the first side-length, the condition for the path of the second side-length, and the condition for the path of the third side-length. In some embodiments, the condition is a set of parameters to evaluate locomotion performance, impose step restrictions, and/or track corticospinal function.

In another exemplary embodiment, a method for quantitative analysis of gait can include constructing a device, generating at least one path along which an animal is forced to walk during at least one walking campaign. The method can further include adjusting at least one condition parameter to generate at least one condition, wherein each condition parameter may be associated with the at least one path and each condition comprises devising a set of condition parameters to cause the animal to perform at least one of a symmetric locomotor task and an asymmetric locomotor task when the animal is forced to perform the at least one walking campaign. The method can further include training the animal on the device by at least acclimating the animal to the at least one condition by causing the animal to perform the at least one walking campaign and/or at least one session of the at least one walking campaign. The method can further include performing the at least one acclimation walking campaign and/or acclimation session until at least one of appropriate or desired inter-stride lengths are achieved for each condition and locomotor standards for each condition are met. The method can further include causing the animal to perform the at least one walking campaign on the device after the training, wherein each of the at least one walking campaigns is derived by generating randomized walking sessions. The method can further include recording data obtained from the at least one walking campaign and performing data analysis of the data.

In some embodiments, constructing the device can further include generating a support framework configured as a square structure to support a plurality of pegs, the support framework comprising a first side-length having a first path, a second side-length having a second path, a third side-length having a third path, and a fourth side-length having a fourth path. In some embodiments, generating the at least one condition can further include generating first condition so that when the animal is forced to perform the at least one walking campaign, the animal performs a symmetric locomotor task, generating a second condition so that when the animal is forced to perform the at least one walking campaign, the animal performs a modified symmetric locomotor task, generating a third condition so that when the animal is forced to perform the at least one walking campaign, the animal performs a left-side asymmetric locomotor task, and generating a fourth condition so that when the animal is forced to perform the at least one walking campaign, the animal performs a right-side asymmetric locomotor task. In some embodiments, generating the locomotor standards for the at least one condition can include ensuring the animal is walking rather than exhibiting other gaiting behavior. In some embodiments, the animal is a rat. In some embodiments, the locomotive standards for the at least one condition can include consistent walking without stops or missteps, minimal head-bobbing exhibited by the rat, a back of the rat being arched and a tail of the rat being raised during locomotion, and each limb of the rat being clearly visible from an orthogonal view of the path at an onset and an offset of a stance phase.

While these potential advantages are made possible by technical solutions offered herein, they are not required to be achieved. The presently disclosed device and method can be implemented to achieve technical advantages, whether or not these potential advantages, individually or in combination, are sought or achieved.

Further features, aspects, objects, advantages, and possible applications of the present invention will become apparent from a study of the exemplary embodiments and examples described below, in combination with the Figures, and the appended claims.

BRIEF DESCRIPTION OF THE DRAWINGS

The above and other objects, aspects, features, advantages and possible applications of the present invention will be more apparent from the following more particular description thereof, presented in conjunction with the following Figures, in which:

FIG. 6 is a block diagram showing an exemplary interconnection between a sensor, a detection unit, an imaging device, and a computational apparatus that may be used with the inventive device.

FIGS. 10A-10C show the relationship between stance or swing phase duration (y-axis) and cycle duration (x-axis) for left-limb favored gait (L6R9) as represented by a regression analysis and a heat map of data point density, an asymmetry index, and diagonality indices (DIs) for four conditions, respectively.

DETAILED DESCRIPTION OF THE INVENTION

The following description is of an embodiment presently contemplated for carrying out the present invention. This description is not to be taken in a limiting sense, but is made merely for the purpose of describing the general principles and features of the present invention. The scope of the present invention should be determined with reference to the claims.

Spinal cord injury and/or stroke often produce asymmetric motor disability that reduces biomechanical efficiency. Rodents can be de facto models for the biomedical research of neural trauma; yet, artisans have failed to provide systems and method that analyze the details of sensorimotor control from rodent behavioral performance. To the knowledge of the inventors, no existing device or method prior to this invention can impose symmetric and asymmetric gaits with the stride lengths that span the range from preferred to critical unstable lengths. The presently disclosed devices and methods can further provide an easy-to-learn task that can challenge stereotypical pathways of the spinal cord and/or the descending neural pathways responsible for the precise limb placement.

Figure 1:
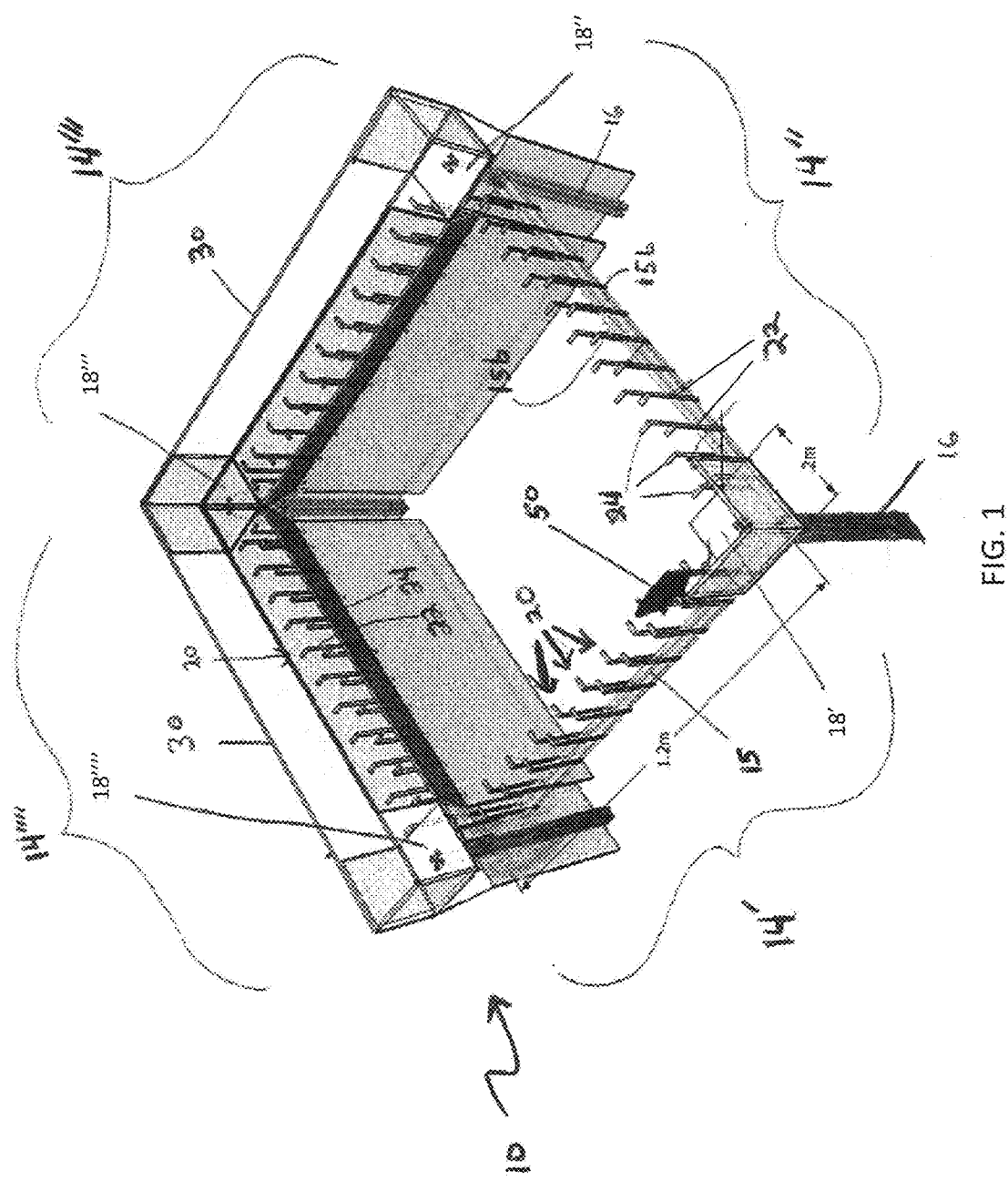
FIG. 1 shows an exemplary support framework that may be used with the inventive device.
Figure 2:
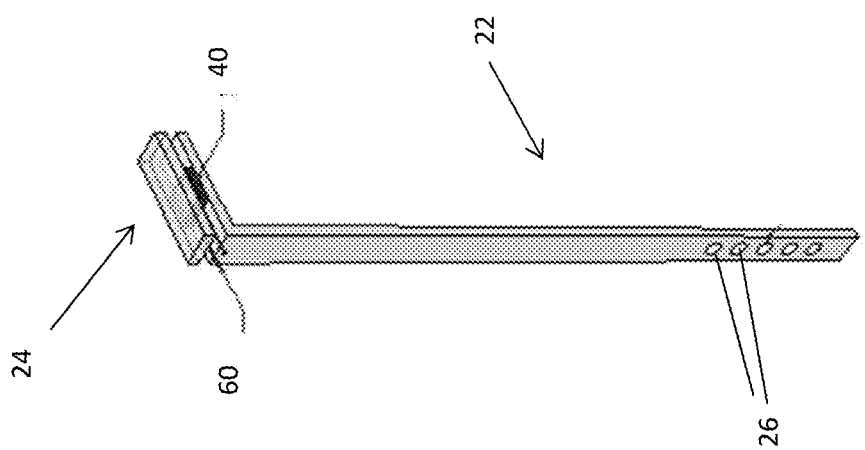
FIG. 2 shows an exemplary peg that may be used with the inventive device.

Referring to FIGS. 1-2, the device can include a support framework 10 structured to support a plurality of pegs 20. The support framework 10 can be further structured as a walkway so as to accommodate an animal walking along a path by stepping on the pegs 20. The path can be defined by the pegs 20 as the "floor" upon which the animal walks and by at least one sidewall 30, directing the animal in at least one direction. In some embodiments, the support framework 10 can be structured to generate a closed-loop walkway. This may include a walkway with a path that feeds back into itself. In further embodiments, the path can be enclosed by a cover (e.g, domed, square, pyramidal, or other shaped structure). The cover can be an enclosure disposed over the walkway where the sides of the dome form the sidewalls 30. Alternatively, the cover can be an enclosure attached to the at least one sidewall 30 of the support framework 10. In at least one embodiment, any portion of the sidewalls 30 and/or cover can be transparent, translucent, or opaque. The transparent and/or translucent portions may be used to enable a user to observe the animal and/or record the animal via imaging and/or video.

Any one peg 20 can include an elongated staff section 22 with a platform section 24. The platform section 24 can extend from a portion of the staff section 22 and provide a surface upon which the animal's foot may be placed. For example, the platform section 24 can extend perpendicularly from the staff section 22. In some embodiments, the peg 20 may form an "L" shape with the long leg of the L being the staff section 22 and the short leg of the L being the platform section 24. Any one peg 20 can be affixed (attached to, secured within, and/or attachable to) a portion of the support framework 10. The affixment of the peg 20 to the support framework 10 can be permanent or temporary. Further, the affixment can be structured to enable adjustment of the placement of the peg 20. Adjusting the placement can include, but is not limited to, adjusting the peg 20 longitudinally (e.g., moving the peg 20 in the z-direction), adjusting the peg 20 laterally (e.g., moving the peg 20 in any one of the x-direction and y-direction), tilting the peg 20, canting the peg 20, rotating the peg 20, etc. (See FIG. 3).

Figure 3:
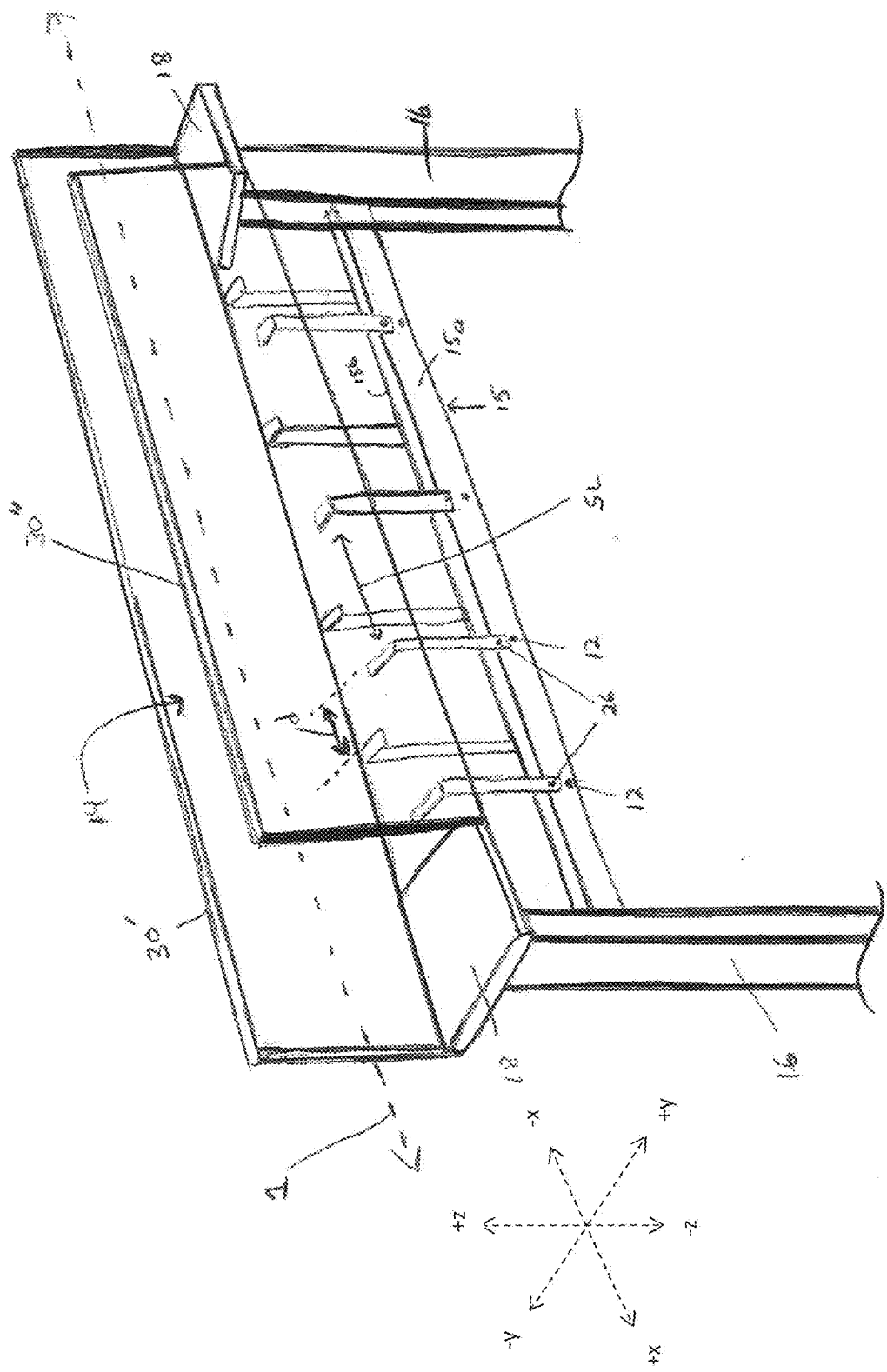
FIG. 3 shows one side-length that may be used with the support structure of FIG. 1.

Referring to FIG. 3, the support framework 10 can include at least one support framework aperture 12 and the staff section 22 of the peg 20 can include at least one peg aperture 26. The peg 20 can be affixed to the support framework 10 by aligning a support framework aperture 12 with a peg aperture 26, wherein a fastener (e.g., pin) can then be inserted through the aligned apertures 12, 26. There can be sets of support framework apertures 12, each set including a plurality of support framework apertures 12. Each peg 20 can also have a plurality of peg apertures 26. The peg 20 can be adjusted longitudinally or laterally by aligning any aperture 26 within the sets of apertures 12. Adjusting the peg 20 longitudinally in the positive z-direction can cause the platform section 24 to be positioned at a higher elevation. Adjusting the peg 20 longitudinally in the negative z-direction can cause the platform section 24 to be positioned at a lower elevation. Similar adjustments can be made in the positive and negative x-directions and y-directions.

Other attachment mechanisms can be used. These may include a pin and detent engagement, a clip engagement, a bayonet-style engagement, a threaded engagement, a telescopic engagement, etc. In some embodiments, placement of the peg 20 can be controlled by motor. For example, the staff section 22 can include a toothed or splined surface. The support framework 10 can include a motor in connection with a wormgear that engages the splined surface and causes the peg 20 to move when the wormgear is caused to rotate. There can be a motor and wormgear for each peg 20. Other actuation means can be used to cause the mechanical and/or automatic adjustment of the placement of any one peg 20. These may include use of a gimbal and electro-mechanical motors, for example. Placement of the peg 20, and in particular placement of one peg 20 relative to another peg 20, can be used to modify gait parameters and/or impose step restrictions (e.g., stride length, intgerlimb phase, incline, etc.). Modifying gait parameters and/or imposing step restrictions can facilitate analyzing details of sensorimotor control, facilitate imposing symmetric and asymmetric gaits with the stride lengths that span a range from preferred to critical unstable lengths, and/or facilitate challenging stereotypical pathways of the spinal cord and/or the descending neural pathways responsible for the precise limb placement Adjusting the placement of any one peg 20 may also facilitate providing perturbations for testing reflexes, such as H-reflexes for example.

Figure 4:
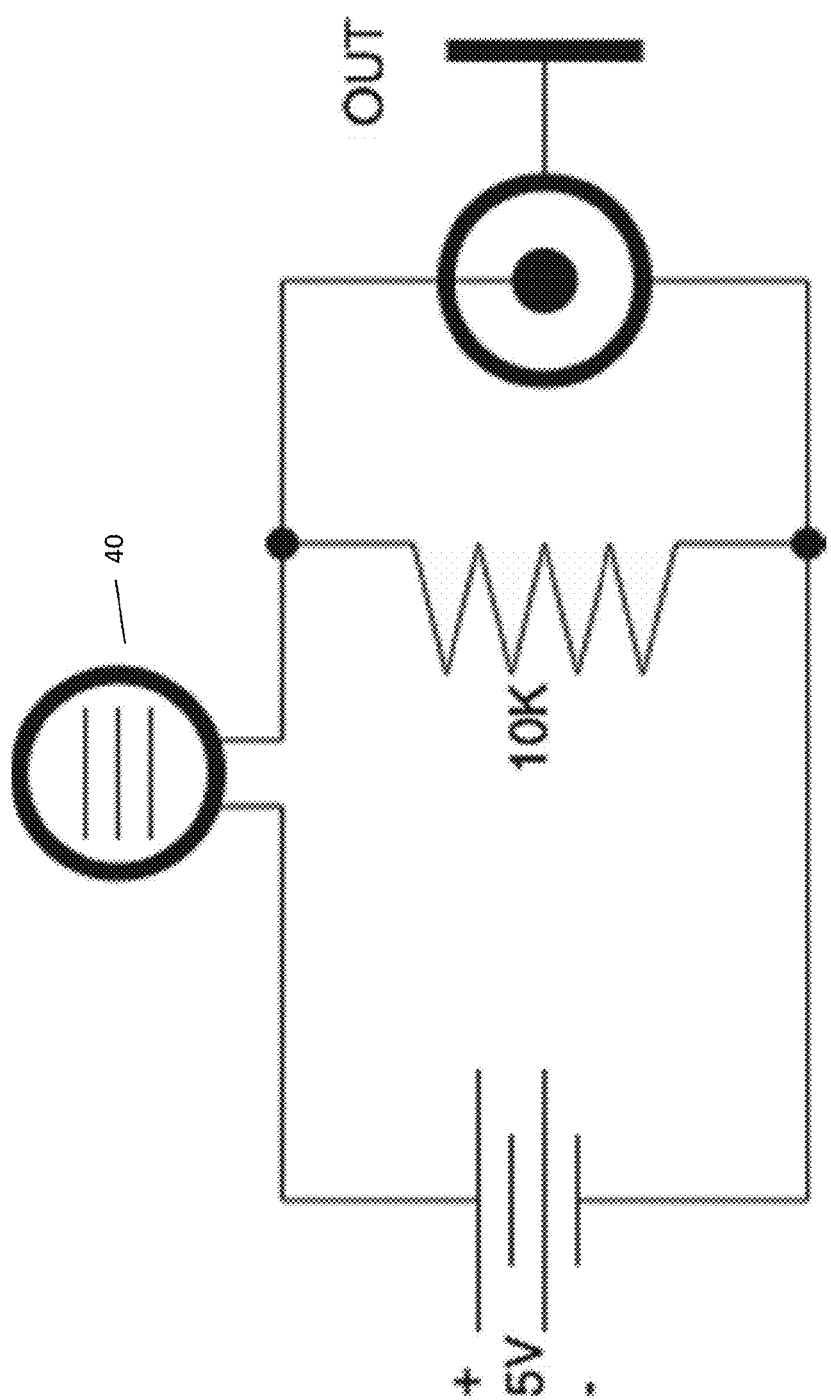
FIG. 4 shows an exemplary electrical circuit that may be used to generate a sensor array.
Figure 5B:
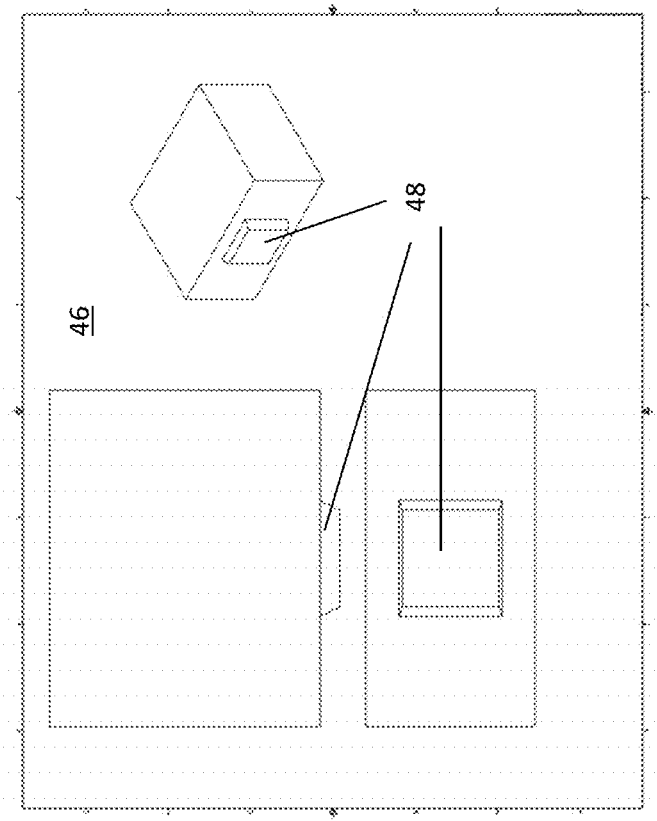
FIGS. 5A-5B show an exemplary sensor enclosure that may be used with the inventive device.
Figure 5A:
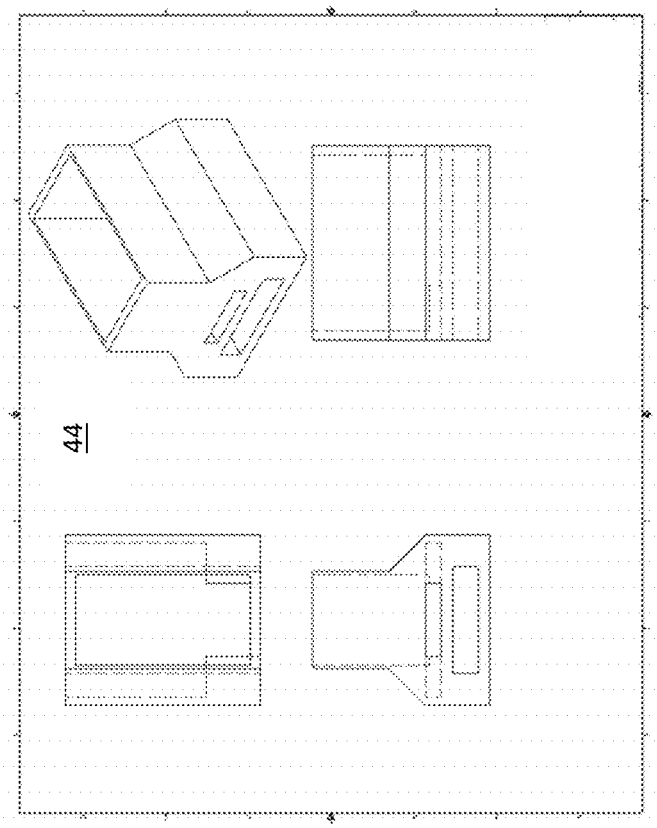

Any one peg 20 can be instrumented with at least one sensor 40 and/or electro-mechanical switch. Any of the sensors 40 can be a contact sensor, a force-sensitive sensor, a pressure sensor, a motion sensor, etc. to detect foot placement by an animal on the platform section 24 of a peg 20. The sensor 40 can be part of a sensor array, an exemplary electrical circuit of which is shown in FIG. 4. The output of the circuit can be a Bayonet Neill-Concelman (BNC) connector to facilitate connection/disconnection with a coaxial cable. The output may further facilitate use with a radio frequency connection. The sensor array 40 can include a two-part sensor enclosure 42, where the enclosure 42 can include a sensor housing pedestal 44 mountable to the platform section 24 of a peg 20 and a rung component 46 fitted to slide into the sensor housing pedestal 44. (See FIGS. 5A-5B). The sensor enclosure 42 can further include an extruded surface 48 to transfer force to the sensor 40. In addition, or in the alternative, kinematic tracking techniques can be used. These may include use of imaging devices 50, such as optical cameras, video recorders, etc. to detect and record foot placement by an animal on the platform section 24 of a peg 20.

Referring back to FIG. 2, in at least one embodiment, each platform section 24 of a peg 20 can include a sensor 40 and/or electro-mechanical switch that may be configured to transmit a signal when the platform section 24 experiences in increase in pressure. The increase in pressure may be due to placement of a foot by the animal on at least a portion of the platform section 24. Any one of the sensors 40 can be in communication with a detection unit 60. The detection unit 60 may be a processor with a non-volatile, non-transitory, memory that can receive and record signals transmitted by the sensor 40. In some embodiments, the signals from the sensor(s) 40 can be analog signals. The analog signals may be sampled with a standard acquisition card (DAQ) for further quantitative analysis.

Use of the sensor(s) 40 and the detection unit(s) 60 can facilitate detection and recordation of walking parameters. Walking parameters can include event data and statistical data associated with the animal's walking campaign. A walking campaign can be one or more walking sessions performed by the animal on the device. Walking parameters can include time of contact with the platform section 24, the number of times the platform section 24 has been stepped on, pressure placed on the platform section 24 by the animal while walking along the walkway, slippage from the platform section 24, etc. Detection and recordation of walking parameters can facilitate evaluation of locomotion performance and tracking of corticospinal function before and after an animal suffers a stroke and/or spinal cord injury.

Any surface of a platform section 24 can include a textured surface and/or coating that may provide a desired contact friction. This may be done to challenge any preferential posture of the animal's postural system. For example, an animal may exhibit a prefer posture of placing more pressure on a left foot than a right foot while conducting a walking campaign. The contact friction of each platform section 24 where the animal is expected to make contact with its right foot can be provided with a contact friction of cf-1, whereas each platform section 24 where the animal is expected to make contact with its left foot can be provided with a contact friction.

Any contact friction cf-i of one platform section 24 can be the same as or different from a contact friction cf-i of another platform section 24.

Referring to FIG. 6, in some embodiments, the device can further include a computational apparatus 70, which may include a computer device and/or computer system. The computational apparatus 70 can include a processor operatively associated with a non-transitory, non-volatile memory that is configured to receive data from at least one of a sensor 40 and/or a detection unit 60 and process the data for analysis.

Some embodiments can include use of at least one imaging device 50 to capture images and/or video of the animal's walking campaign. This may include use of a high definition camera and/or video recorder. The imaging device(s) 50 can be separate from the support framework 10 or be affixed thereto. The same affixment means used for the pegs 20 can be used for the imaging device(s) 50. In some embodiments, the imaging device 50 captures images and/or video of the animal's walking campaign by viewing the animal through the transparent sidewall(s) 30. In other words, at least one imaging device 50 can be located at or near a sidewall 30 to record at least a portion of the walking campaign through the sidewall 30. The imaging device(s) 50 can be configured to either produce digital recordings and/or generate digital representations of optical recordings. The imaging device(s) 50 can be in communication with the computational apparatus 70 so as to transmit the digital recordings and/or digital representations of optical recordings to the computational apparatus 70 for further analysis. The imaging device(s) 50 can further include a gimbal and electro-mechanical motors to cause the imaging device(s) 50 to rotate, pitch, and/or roll. The imaging device(s) 50 can further include motion sensors and automatic focusing software to cause the imaging device(s) 50 to follow the animal as it performs its walking campaign and to automatically focus the lens of the imaging device(s) 50.

Any of the communication links between components (sensors 40, imaging devices 50, detection units 60, and/or computational apparatuses 70) of the invention can be via wireless and/or hardwire links. Where the communication between any two components is wireless, the components in communication with each other may include transmitters, receivers, and/or transceivers to facilitate such communication.

Referring back to FIGS. 1-3, in at least one embodiment, the support framework 10 can be structured as a square structure, where the square structure can have four side-lengths 14 (a first side-length 14', a second side-length 14", a third side-length 14''', and a fourth side-length 14''''). The support framework 10 can be supported by at least one pillar 16. A pillar 16 can be located at each corner of the square structure. Each side-length 14 can include a beam 15 having an inner edge 15a and an outer edge 15b. A plurality of pegs 20 can be affixed to at least one side-length 14. For example, each staff section 22 can be affixed to the beam 15 of the side-length 14 so that the platform section 24 extends upward and away from the beam 15. Any side-length 14 can include a plurality of pegs 20 affixed to the side-length beam 15 of that side-length 14. Any one peg 20 can be affixed to an inner edge 15a or an outer edge 15b of the side-length beam 15 of that side-length 14. Each peg 20 can be affixed to the side-length beam 15 of that side-length 14 so that the platform section 24 extends upward and away from the beam 15.

Any one side-length 14 can further include at least one sidewall 30. The sidewall 30 can be a rectangular object that spans a length of the side-length 14 and have a height that effectively acts as a wall to guide the animal along the path that is along the side-length 14. For example, a sidewall 30 can be a rectangular sheet of metal, wood, glass, plastic, plexiglass, acrylic, fiberglass, etc. The support framework 10 can include a first sidewall 30' affixed to an outer edge 15a of a beam 15 of a side-length 14. The support framework 10 can include a second sidewall 30" affixed to an inner edge 15b of a beam 15 of a side-length 14. The same affixment means used for the pegs 20 can be used for any sidewall 30.

Any path of the support framework 10 can include a rest platform 18. In at least one embodiment, at least one corner of the support framework 10 can include a rest platform 18. The rest platform 18 may include a square or rectangular plate that is large enough to allow the animal to stand upon securely in a stationary position to allow the animal to rest. The rest platform 18 can be made of any material that is used for the support framework 10. A first sidewall 30' can be affixed outer edges of any of two opposing rest platforms 18 so that the first sidewall 30' spans a length of the side-length 14 between the two opposing rest platforms 18. A second sidewall 30" can be attached to inner edges of any of two opposing rest platforms so that the second sidewall 30' also spans the length of the side-length 14 between the two opposing rest platforms 18. Thus, each side-length 14 can be provided with a first sidewall 30' and/or a second sidewall 30", each spanning the length of the side-length 14 between the two opposing rest platforms 18.

A volume of space between the plurality of platform sections 24 arranged along a side-length 14 and the sidewall(s) 30 of the side-length 24 can define the path. The plurality of pegs 20 of any side-length 14 can be staggered so that each consecutive peg 20 is affixed to the inner and outer edges 15a, 15b, alternatively, of the side-length beam 15. In other words, a first peg 20 may be affixed to the inner edge 15a of the side-length beam 15, a second peg 20 may be affixed to the outer edge 15b of the side-length beam 15, a third peg 20 may be affixed to the inner edge 15a of the side-length beam 15, and so on.

The plurality of pegs 20 of any side-length 14 can be configured so that each platform section 24 has a space (d) between it and an adjacent platform section 24. The spacing (d) between two adjacent platform sections 24 can be the same as or different from any other spacing (d) between any other two adjacent platform sections 24. The height-differential (h) between two adjacent platform sections 24 can be the same as or different from any other height-differential (h) between any other two adjacent platform sections 24. Any of the peg 20 placements (height, lateral placement, tilt, angle, etc.) can be adjusted. It is contemplated for the animal to walk along at least one side-length 14 by stepping on the platform sections 24 to gain footing. For example, the animal can start at the first rest platform 18' and be caused to walk along a first path of the first side-length 14' by stepping on the platform sections 24 until it reaches the second rest platform 18". The animal can continue to walk along a second path of the second side-length 14" until it reaches the third rest platform 18'". The animal can continue to walk along a third path of the third side-length 14'" until it reaches the fourth rest platform 18''''. The animal can continue to walk along a fourth path of the fourth side-length 14'''' until it reaches the first rest platform 18'.

Figure 7:
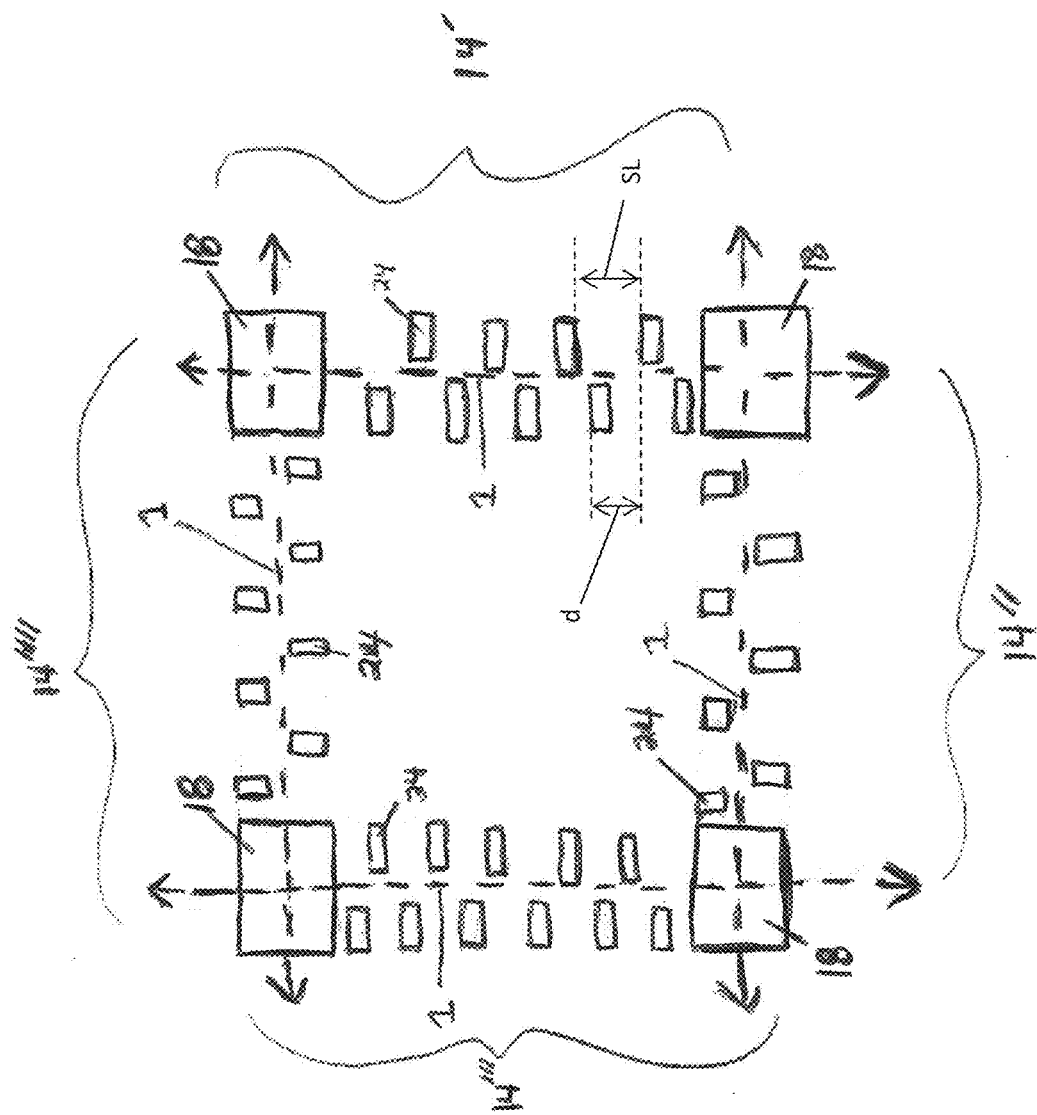
FIG. 7 is a top view of the support framework of FIG. 1.
Figure 8:
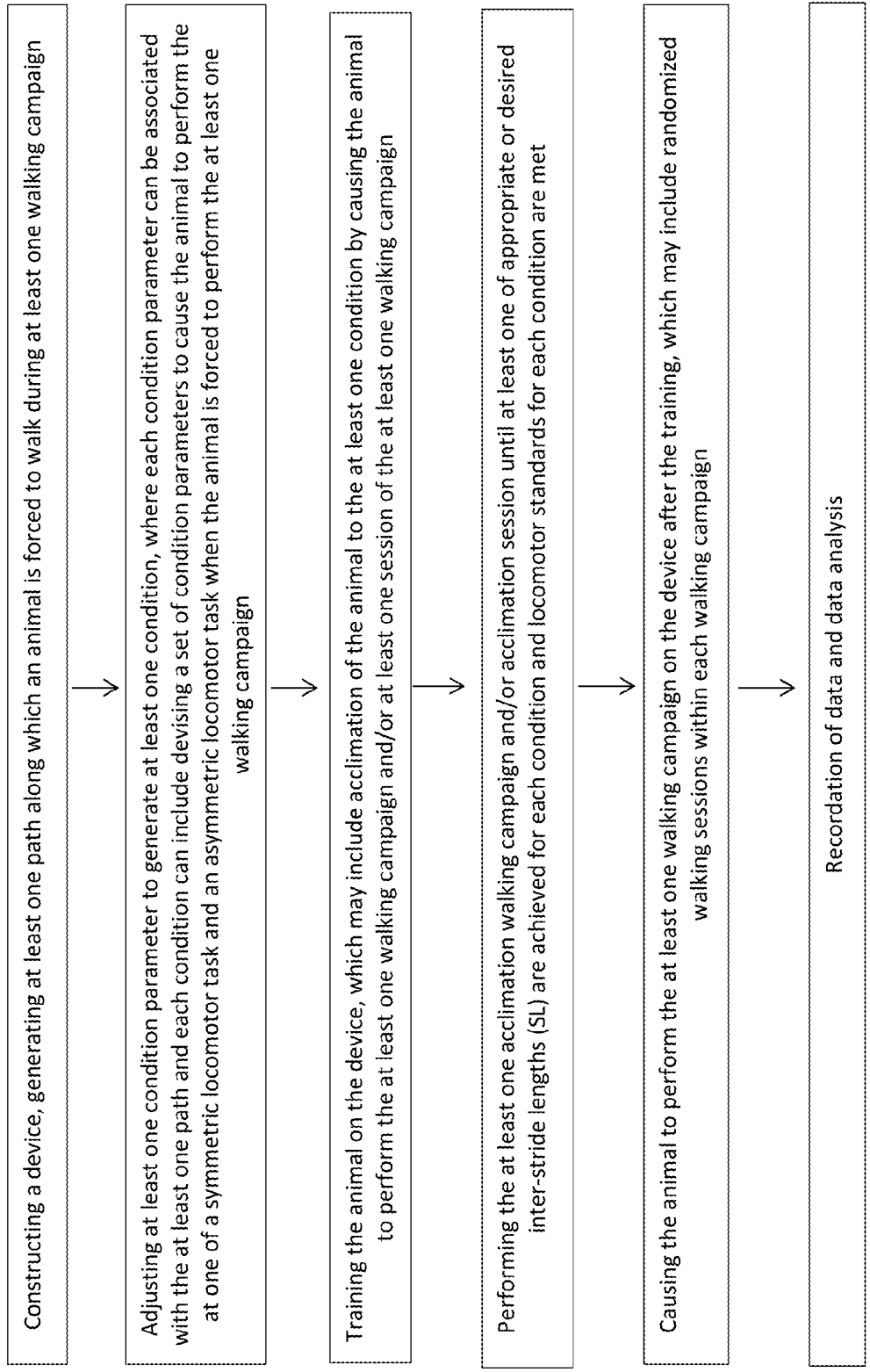
FIG. 8 shows a flow diagram demonstrating an exemplary method of use of the inventive device.

Referring to FIGS. 3 and 7, in some embodiments, the pegs 20 arranged within a path can be configured so that the platform sections 24 provide salutary support for a left and a right foot. For example, each path can include a plurality of pegs 20 in a linear arrangement along the path. The path can further include a central pathway 1 running along its center between distal ends of a side-length 14. At least one peg 20 of the plurality of pegs 20 can be arranged such that its platform section 24 is positioned to a first side of the central pathway 1. Further, at least one peg 20 of the plurality of pegs 20 can be arranged such that its platform section 24 is positioned to a second side of the central pathway 1. When the animal is in the path and facing along a direction of the central pathway 1, the first side can be the same as the anatomical left side of the animal, and the second side can be the same as the anatomical right side of the animal. In some embodiments, the plurality of pegs 20 in the linear array can be arranged such that each adjacent platform section 24 alternates from being positioned on the first side to the second side. In other words, the plurality of pegs 20 may be arranged such that the first platform section 24 is on the first side, the second platform section 24 is on the second side, the third platform section 24 is on the first side, and so on. This may be done to facilitate a salutary flooring for walking. This may also force the animal to place a left foot on a first-side positioned platform section 24 and to place a right foot on a second-side positioned platform section 24 as the animal walks along the path.

With an alternating first-side and second-side platform section 24 arrangement between adjacent pegs 20, a distance between consecutive platform sections 24 on a same side can define a stride length (SL). For example, the distance between the first platform section 24 and the third platform section 24 can be the SL between the first and third platform sections 24. The SL between any two consecutive platform sections 24 can be the same as or different from the SL between any other two consecutive platform sections 24. Further, the SL between any one of the first-side positioned platform sections 24 can be the same as or different from the SL between any one of the second-side positioned platform sections 24. Note, the spacing (d) may be referred to as inter-stride length.

Any of the supportive framework 10, rest platforms 18, sidewalls 30, and/or the pegs 20 may be fabricated from a rigid, support-bearing material. This can include, but is not limited to metal, wood, plastic, glass, acrylic, etc. In at least one embodiment, any portion of the support framework 10, rest platforms 18, sidewalls 30, and/or pegs 20 can be aluminum (e.g., 80/20 aluminum). A material of the support framework 10 can be the same as or different from a material of the rest platforms 18, sidewalls 30, and/or pegs 20. Any material used for one peg 20 can be the same as or different from a material of another the peg 20. The support framework 10, rest platforms 18, sidewalls 30, and/or pegs 20 can be configured into a variety of shapes with a variety of dimensions to accommodate different animals and research paradigms. For example, the support framework 10 can be a rectangular structure with only one path. As another example, the support framework 10 can be a circular structure with one circular path, or one spiral path. Further, any of the paths can be straight, curved, zigzag, etc.

The distances (d), height-differentials (h), SL, contact friction, other peg 20 placement parameters, and additional variables can be used to set at least one condition. A condition can be a set of parameters used to evaluate locomotion performance, impose step restrictions, and/or track corticospinal function. For instance, a first set of parameters can be a first condition, a second set of parameters can be a second condition, etc. A first condition may be a set of parameters that when the animal is forced to perform a walking campaign, causes the animal to perform a symmetric locomotor task. A second condition may be a set of parameters that when the animal is forced to perform a walking campaign, causes the animal to perform a modified symmetric locomotor task. A third condition may be a set of parameters that when the animal is forced to perform a walking campaign, causes the animal to perform a left-side asymmetric locomotor task. A fourth condition may be a set of parameters that when the animal is forced to perform a walking campaign, causes the animal to perform a right-side asymmetric locomotor task. In some embodiments, each side-length 14 of the square structure can be individually configured to generate a condition-specific path. For example, the first side-length 14' may be configured to generate a first condition-specific path, the second side-length 14" may be configured to generate a second condition-specific path, the third side-length 14'" may be configured to generate a third condition-specific path, and the fourth side-length 14'''' may be configured to generate a fourth condition-specific path.

In an exemplary embodiment, the device can be used with rats as the animals to be tested upon. The device can include a support framework 10 structured as an open-top plastic box braced with aluminum supports 16 at each corner. Each aluminum support can have approximate dimensions of 155×104 cm. Top edges of the box can be braced with aluminum bars grooved on both sides to facilitate alternate peg 20 placement. Peg 20 placement can be along a perimeter of the box. Each consecutive peg 20 on the same side may define a SL. A rest platform 18 that is approximately 20 cm×20 cm can be placed at each corner (four total), separating the conditions represented on each side-length 14. Each side-length 14 can be a distance that is sufficient for the inclusion of the distance traversed by a single rat step cycle, as this distance may define the length of the walkway. For example, each side-length 14 can be approximately 120 cm. Each side-length 14 can further include a first sidewall 30' along an outer edge 15a of each side-length 14. The sidewalls 14 can be transparent. Portions of the sidewalls 14 at each corner can be opaque. Pegs 20 made of aluminum with approximate dimensions of 20 cm×1 cm×0.5 cm and with a foot placement platform 24 measuring approximately 2.5 cm can be secured to the grooved bars. This can be done by using sliding inside brackets through machined holes located at a same distance to ensure level horizontal placement of each platform 24. Relative placement of the pegs 20 and/or platforms 24 may be achieved with use of a screwdriver and a ruler. A 1 cm peg width, or a 1 cm platform section 24 width, can correspond approximately to an average rat paw size. A platform section 24 that is thinner or wider than 1 cm may be either uncomfortable or increase foot placement variability. A high definition camera 50 with a sampling rate of at least 60 Hz can be used. The location of the high definition camera 50 can be such that the placement of limbs on pegs 20 is unobstructed. The high definition camera 50 can be configured to point perpendicularly to the walkway with the field of view covering about 7 steps.

The device can be used to detect and record walking parameters, and further facilitate evaluation of locomotion performance of the animal conducting a walking campaign. A method of using the device can include constructing the device, generating at least one path. The method can further include adjusting at least one condition parameter to generate a condition. A separate condition can be generated for each path. In some embodiments, a plurality of paths can be generated. The plurality of paths can include a first path, a second path, a third path, and a fourth path. Generating the first path can include defining the first path by the first condition. The first condition can include devising a set of parameters to cause the animal to perform a symmetric locomotor task when the animal is forced to perform a walking campaign. Generating the second path can include defining the second path by the second condition. The second condition can include devising a set of parameters to cause the animal to perform a modified symmetric locomotor task when the animal is forced to perform a walking campaign. Generating the third path can include defining a third path by the third condition. The third condition can include devising a set of parameters to cause the animal to perform a left-side asymmetric locomotor task when the animal is forced to perform a walking campaign. Generating the fourth path can include defining the fourth path by the fourth condition. The fourth condition can include devising a set of parameters to cause the animal to perform a right-side asymmetric locomotor task when the animal is forced to perform a walking campaign.

The method can further include training the animal on the device. The training may include acclimation of the animal to the at least one condition by causing the animal to perform at least one walking campaign and/or at least one session of a walking campaign. A walking campaign can be traversing a path for a minimal amount of times. The acclimation sessions can continue until appropriate or desired inter-stride lengths are achieved for each condition. The appropriate or desired inter-stride lengths may be set by the experimenter, and can be based on the test being performed, the condition, the type of animal, etc. The acclimation sessions can further continue until locomotor standards for each condition are met. The locomotor standards may vary from animal to animal, but the locomotor standards should be set such that the animal is clearly walking rather than exhibiting other gaiting behavior (e.g., walking as opposed to galloping). The locomotor standards for rats, as an example, can include, but are not limited to: 1) consistent walking without stops or missteps; 2) minimal head-bobbing is exhibited by the animal; 3) the back is arched and the tail is raised during locomotion; and, 4) each limb is clearly visible from an orthogonal view of the walkway at an onset and an offset of a stance phase.

The method can further include causing the animal to perform walking campaigns on the device after training. This can include randomized walking sessions within each walking campaign. The method can further include recordation of data and data analysis. The recordation of data can include segmenting walking bouts (e.g., lengths along a path where the animal is walking) from other gaiting bouts (e.g., lengths along a path where the animal is gaiting in a manner other than walking). Data associated with the non-walking bouts may be excluded from the data analysis. The recordation of data can include identifying onsets and offsets of kinematic phases. This can include identifying a time of stance onset and a time of offset for each limb. Analyzing the data can include calculating a duration of swing phase, which can be a time remaining between two consecutive kinematic stance onsets. The analyzing the data can further include graphical representations of data and statistical analysis (correlations, variance, linear regression, etc.). In some embodiments, the slope of a linear regression equation generated from a linear regression analysis can be used to represent an amount of change in phase duration as a function of a change in speed of locomotion. The analyzing the data can further include other statistical and numerical analyses to generate variables representing at least one of asymmetry index, horizontal difference, and vertical asymmetry. In the case of four-legged animals, the statistical variables can further include forelimb asymmetry, hind-limb asymmetry, left forelimb-hind-limb asymmetry, right forelimb-hind-limb asymmetry, diagonality indices, etc.

In an exemplary embodiment, the method can facilitate employment of the device for many uses. These may be imposing different locomotor behaviors for basic science research. This may also be evaluating movement impairment in rodents used to model neurological, psychological, and/or musculoskeletal conditions. In particular, the device may be used for: tracking the corticospinal function before and after stroke or spinal cord injury; tracking progression of diseases that cause movement impairment, e.g. Parkinson's, Alzheimer's, ALS symptoms, blast trauma to cortex; and/o, tracking progression of movement disabilities in geriatric research.

Use of the device can solve and address the gap in the availability of behavioral research tools in rodents that focus on the movement evaluation. For example, the presently disclosed device and methods of use may enable researchers to impose a variety of behavioral tasks that range from stereotypical locomotion to precise limb placement in rodents using a task that may require minimal or no training of animals. Other uses may include additional development of tracking and analysis tools.

The method of use can include a precise foot-placement locomotor task that evaluates cortical inputs to the spinal CPG. In addition, the device can be used to impose symmetrical and asymmetrical locomotor tasks, which may be configured to mimic lateralized movement deficits. Using the device, the inventors have discovered that shifts from equidistant inter-stride lengths of 20% can produce changes in the forelimb stance phase characteristics during locomotion with preferred stride length. Furthermore, the asymmetric walkway of the device can allow for measurements of behavioral outcomes produced by cortical control signals. These measures may be relevant for the assessment of impairment after cortical damage.

The method can be a low-cost method for assessing the activity of descending cortical inputs in the motor system of quadruped animals based on a precise stepping locomotor task. The task can be designed to challenge the motor cortex by imposing demands on foot placement over a natural range of walking speeds. In addition, foot-placement requirements may be manipulated to preferentially challenge the left or right side of the animal's motor system. In a similar locomotor task, Metz & Whishaw (2009) examined the rates of failure, the number of missed steps on irregular rung walkway, in rats. Yet, the inventive method can be used to detail the quality of phase control in "successful" steps[18].

Referring to FIGS. 9A-12B, an exemplary method was used as a training paradigm that employed the analysis of phase adjustments of the average adult Sprague-Dawley rat. All procedures used within the exemplary training paradigm were performed in accordance with the Institutional Animal Care and Use Committee (IACUC) and Office for Laboratory Animal Welfare (OLAW) at West Virginia University School of Medicine and abided by the National Institutes of Health guidelines for the use of experimental animals. The inventors employed the analysis of phase duration characteristics[17] that describes the relationship between the duration of swing or stance phases as a function of cycle duration in each step. The obtained linear regression model was then further described with an analysis of asymmetry across all limbs.

Figure 9B:
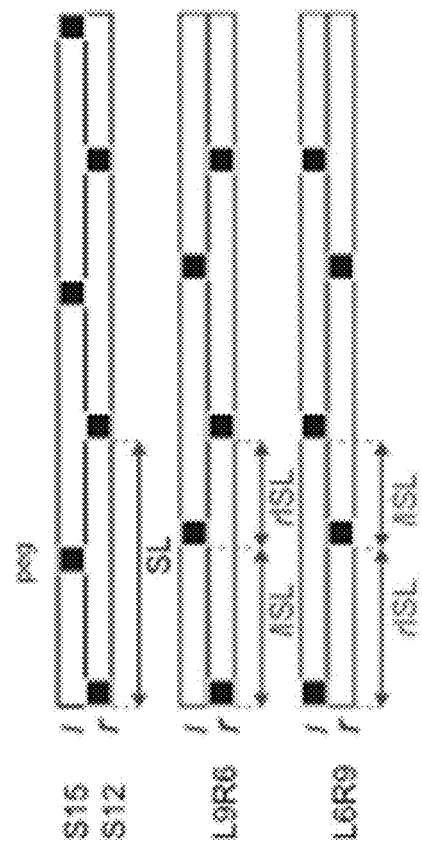
FIGS. 9A-9B show a schematic of a walkway that may be used for symmetric and asymmetric gait tasks, and a peg arrangement setting the right (rISL) and left (lISL) inter-stride lengths in relation to the stride length (SL), respectively.
Figure 9A:
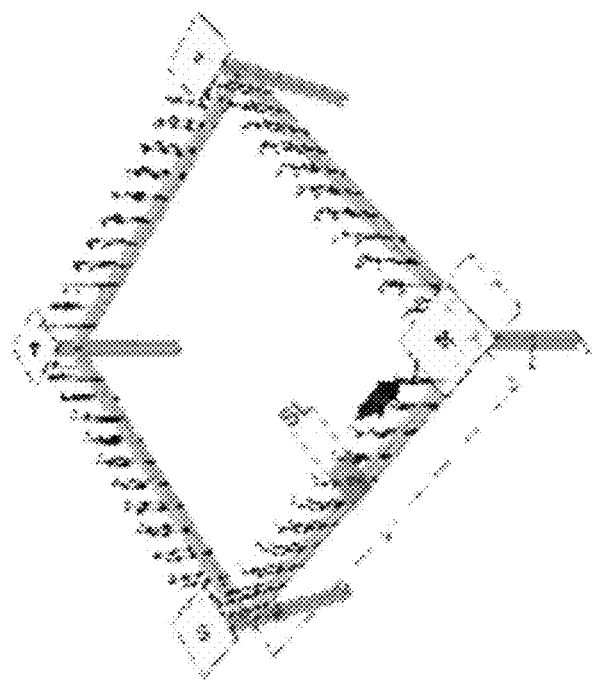

1. Exemplary Equipment Setup that May be Used with the Exemplary Training Paradigm Method Referring to FIGS. 9A-9B, FIG. 9A shows a schematic of the walkway used for the symmetric and asymmetric gait tasks and FIG. 9B shows the peg 20 arrangement setting the right (rISL) and left (lISL) inter-stride lengths in relation to the stride length (SL). The four conditions includes a symmetrical control locomotor task with 15 cm SL (SL15), a symmetrical locomotor task representing a 20% reduction in SL and preferred speed (SL12), a left limb preferred (L9R6), and a right limb preferred (L6R9) locomotor task.

1.1. Construct the asymmetric walkway as an open-top plastic box 10 braced with aluminum supports 16 at each corner measuring 155 cm×104 cm. Brace the top edges of the box 10 with aluminum bars grooved on both sides to allow for alternate peg 20 placement, along the perimeter of the box 16, so that each consecutive peg 20 on the same side defines the SL.

1.2. Place a 20 cm×20 cm platform 18 on each corner (four total) separating the conditions represented on each side 18. This distance should be sufficient for the inclusion of the distance traversed by a single rat step cycle.

1.1.1. Use pegs 20 made of aluminum with dimensions of 20 cm×1 cm×0.5 cm. Bend the top of each peg 20 at 2.5 cm from the tip to produce a foot placement platform 24.

1.1.2. Secure the pegs 20 to the grooved bars using sliding inside brackets through machined holes at the same distance to ensure level horizontal placement. Adjust positions using a screwdriver and a ruler. Use a 1 cm peg width that corresponds approximately to the average rat paw size; thinner or wider pegs are either uncomfortable or increase the foot placement variability.

1.3. Manipulate the peg 20 placement on each side to produce one of three precise stepping challenge conditions.

1.4. Produce a symmetric locomotor task with a 15 cm stride length (SL15) by setting the left inter-stride length (lISL) and right inter-stride length (rISL) to the half of stride length (7.5 cm). An additional symmetric condition (SL12) is imposed by lISL and rISL lengths of 6.0 cm.

1.5. Produce the asymmetric tasks by changing the distance between pegs 20 on the left and right sides, termed the inter-stride length. To challenge the motor system asymmetrically, change the lISL and rISL by 20% to impose short inter-stride lengths either on the left (L6R9 condition) or on the right (L9R6) side. The 1.5 cm perturbations impose an lISL of 6 cm and rISL of 9 cm for the L6R9 condition, or an lISL of 9 cm and a rISL of 6 cm for the L9R6 condition.

1.6. For rats, keep the stride length for all conditions except for SL12 at a preferred 15 cm.

1.7. For convenience, assign each long side of the walkway an asymmetric condition favoring either the left or the right side of the subject, while reserving the two short sides for the symmetric control condition.

1.8. Setup a high definition camera 50 with a sampling rate of at least 60 Hz so that the placement of limbs on pegs 20 is unobstructed with the camera 50 pointing perpendicularly to the walkway and with the field of view covering about 7 steps. The first and last steps in proximity to platforms 24 are ignored.

2. Exemplary Training on Device that May be Used with the Exemplary Training Paradigm Method 2.1. Please use standard training resources, e.g. NIH Training in Basic Biomethodology for Laboratory Rats, to familiarize with general behavioral training of rodents.

2.2. In the beginning of training, acclimate subjects by placing and rewarding them on the 20×20 cm platform 18 for at least 5 min. Then, guide the animals across a peg 20 arrangement with a 1 cm inter-stride length to the next platform 18 by the presentation of a food reward. Reward animals verbally and with petting for reaching the platform 18.

2.3. After 5 training runs, space the pegs 20 an extra 1-2 cm apart and perform the next 5 training runs. The number of repetitions listed herein is sufficient to produce statistically appropriate sample size (20-35 steps).

2.1.1. If the animal acquires the task more slowly as judged by consistency of stepping (no stopping) and posture (arched back), then focus training on the strengthening of these skills at the short stride lengths (S12) before resuming training on the long strides (S15) eventually approaching the desired stride length.

2.1.2. If the new spacing induces anxiety or discomfort with the task, readjust the pegs 20 to the previous setting and repeat the training paradigm.

2.1.3. Proceed with this training until the appropriate inter-stride lengths are achieved for the four conditions and locomotor standards are met. In our experience, the rats responded well to vocal encouragement as cues for initiating a trial. The testing can be done on the same day as training provided the subjects are motivated to perform the task.

Note: The locomotor standards are as follows: walking is consistent and does not involve stops or missteps; head-bobbing is minimal; the back is arched and the tail is raised during locomotion; each limb is clearly visible from an orthogonal view of the walkway at the onset and offset of the stance phase. This selection process was essential as the present study focused only on walking rather than other gaiting behavior.

3. Exemplary Testing and Data Analysis that May be Done with the Exemplary Training Paradigm Method Referring to FIGS. 10A-10C, FIG. 10A shows the relationship between stance or swing phase duration (y-axis) and cycle duration (x-axis) for left-limb favored gait (L6R9) as represented by the regression analysis and a heat map of data point density. FIG. 10B shows asymmetry index calculated as shown in Equations (1) and (2), where r, l, a and p are slopes of the stance phase linear regressions for the right, left, anterior and posterior limbs, respectively. $lAI_v$, $rAI_v$, $aAI_h$ and $pAI_h$ are left-vertical, right vertical, fore-horizontal and hind-horizontal asymmetry indices, respectively, calculated for all four conditions. FIG. 10C shows the diagonality indices (DIs) calculated as shown in Equation (3) for all four conditions lF, rF, lH and rH, which are left forelimb, right forelimb, left hind-limb, and right hind-limb stance phase linear regression slopes, respectively. The phase characteristics were represented with the stance phase linear regressions using the slope-intercept equations. The insets correspond to the left forelimb (LF), right forelimb (RF), left hind-limb (LH) and right hind-limb (RH) heat maps.

3.1. Test animals on S12, S15, L9R6, and L6R9 tasks (described in section 1.5) using randomized session design. Use breaks to avoid adaptation within a task.

3.2. Import video recordings without re-sampling into video editing software and select only the walking bouts for further analysis.

3.3. Mark onsets and offsets of kinematic phases in video recordings from each subject.

3.4. Here, use the custom software called videoa written in Matlab® to manually identify the time of stance onset and offset for each limb on a frame-by-frame basis, where stance onset is indicated by the loss of motion blur associated with the limb placement on a peg, and stance offset, occurring at the onset of limb lift-off, is indicated by the first evidence of motion blur.

3.5. Calculate the duration of swing phase as the time remaining between two consecutive kinematic stance onsets. Exclude any behavior not consistent with overground quadrupedal walking, e.g. when gait contains a double swing phase (both forelimbs or hind-limbs off the ground), from proceeding analyses.

3.6. Plot the duration of each phase as a function of the corresponding step cycle duration. Capture the relationship with the linear regression model (Tphase=B1+B2*Tc) obtained for each limb, where Tc is cycle duration, Tphase is either Te extensor-related stance or Tf, which is the flexor-related swing, and B1 and B2 are empirical constants (offset and slope) of the regression model.

Note: The slope (B2) represents the amount of change in phase duration with the change in speed of locomotion.

3.7. Use Equations 1 and 2 for each limb to calculate asymmetry index (AI). Both equations have the same form of a simple ratio that normalizes the difference of two values to their sum.

$$AI_h = (r-1)/(r+1) \quad \text{Equation (1):}$$

$$(a-p)/(a+p) \quad \text{Equation (2):}$$

3.1.1. Using Equation 1, calculate the horizontal difference ($AI_h$) that uses the difference between slopes of stance modulation left (l) and right (r) limbs. Similarly, calculate the vertical asymmetry ($AI_v$) using the slopes from front/anterior (a) and back/posterior (p) limbs. The result of applying these two equations is the dataset of 4 x-y points corresponding to 1) forelimb asymmetry, $aAI_h$; 2) hind-limb asymmetry, $pAI_h$; 3) left forelimb-hind-limb asymmetry, $lAI_v$; 4) right forelimb-hind-limb asymmetry, $rAI_v$.

3.1.2. Plot these values as a patch (see FIG. 10B) for the visual representation of asymmetry across all limbs.

3.8. Calculate diagonality indices (DI) to assess diagonal coupling between parameters of a forelimb and its contralateral hind-limb by using Equation 3 (see FIG. 10C).

$$AI_h = [(rF+lH)-(lF+rH)]/[rF+lH+lF+rH]. \quad \text{Equation (3):}$$

3.9. Test the DI, as well as the difference of four AIs between conditions of opposing asymmetry ($\Delta AI=|AIL9R6-AIL6R9|$) for statistical significance using a one-way ANOVA with the post-hoc comparison of means analysis.[19]

FIGS. 10A-10C show the analysis of asymmetry during the locomotor tasks for a single representative subject. The values were calculated for all conditions using Equation 1 and 2 from all subjects individually and from composite data of 8 female Sprague-Dawley rats (250-400 g, see FIGS. 11A-11B). Generally, the modulation of the forelimb stance phase was lesser for the side to which the locomotion condition was favored (short ISL), consistent with the notion that the stance phase on the preferred side (long ISL) tended to occupy a greater portion of the step cycle as compared to the favored limb as the speed of locomotion decreases.

The difference between corresponding asymmetry indices obtained from conditions L9R6 and L6R9 ($\Delta AI$) were tested with a one-way ANOVA ($\alpha=0.05$) and post-hoc t-tests with conservative Bonferroni correction (adjusted $\alpha=0.0125$) using anova1 and multcompare functions in Matlab®. Overall, the difference between groups was significant (p=0.002). The anterior horizontal asymmetry index ($\Delta aAI_h$) corresponding to the asymmetry between forelimbs was significantly different (p=0.006) between the left-favored (L6R9) and the right-favored (L9R6) conditions. The difference between the conditions for the right vertical asymmetry index ($\Delta rAI_v$) showed a trend, but it was not significantly different from zero (p=0.031, $\alpha=0.0125$). Similarly, the inventors found a significant difference (p=0.020, $\alpha=0.05$) in the diagonality index (DI) between two asymmetric conditions. ANOVA testing found no differences between DI in different tasks, but there was only a single post-hoc t-test, which required no additional alpha correction.

Figure 11B:
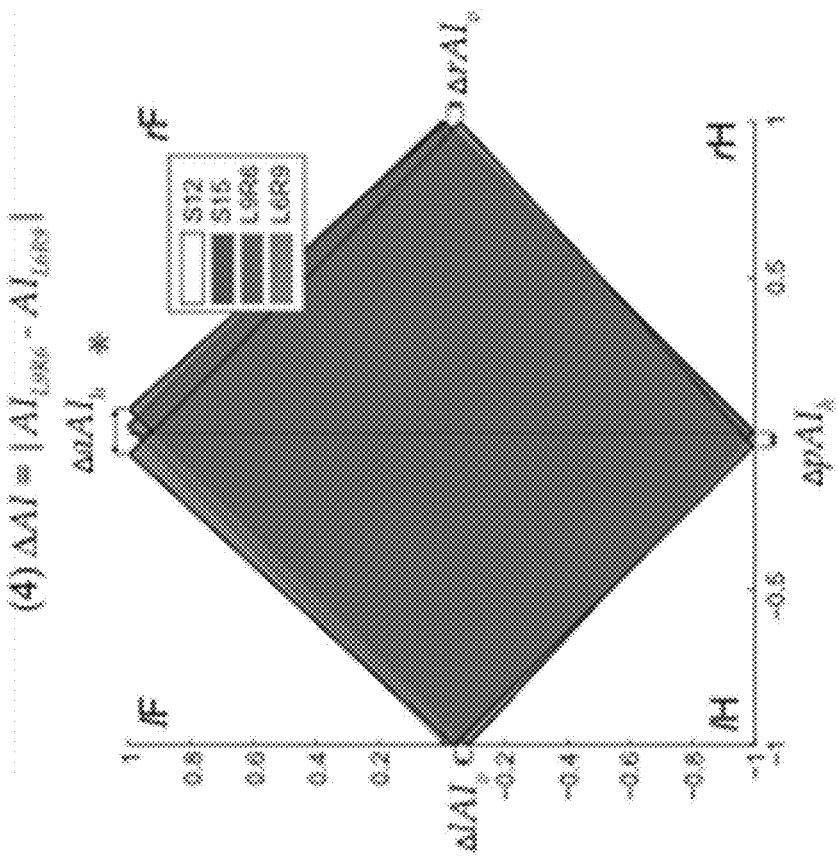
FIGS. 11A-11B show a heat map representing the distribution of stance or swing versus cycle duration, and a calculated the asymmetry index, respectively.
Figure 11A:
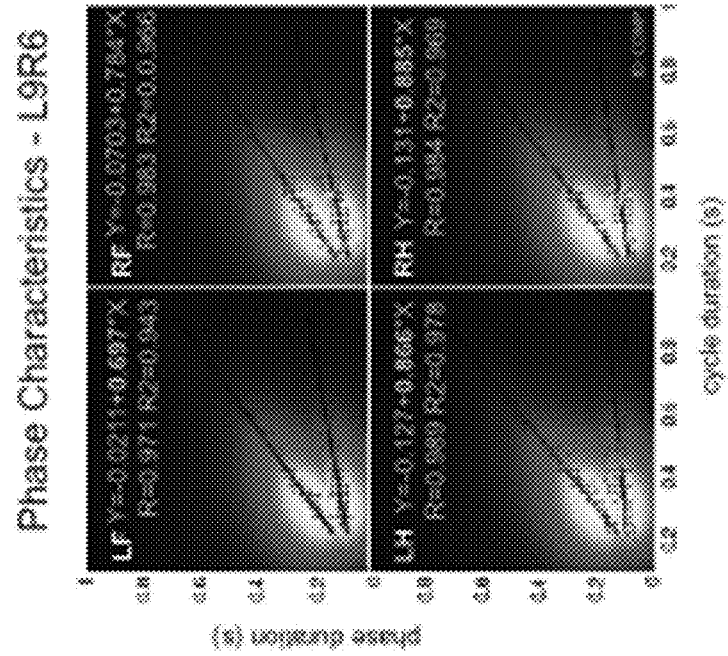

Referring to FIGS. 11A-11B, FIG. 11A shows a heat map representing the distribution of stance or swing versus cycle duration for left-limb favored gait (L9R6). The phase characteristics of the stance phase linear regression were calculated, and are represented by the slope-intercept formula inset. FIG. 11B shows the asymmetry index calculated. $\Delta lAI_v$, $\Delta rAI_v$, $\Delta aAI_h$ and $\Delta pAI_h$—left-vertical, right vertical, anterior-horizontal and posterior-horizontal asymmetry index differences, respectively, calculated for all four conditions as described in Equation 3 by subtracting the corresponding asymmetry indices of the right-favored gait (L6R9) from the left-favored gait (L9R6) conditions. Asterisk—statistical significance as calculated by the Bootstrap method.

Figures 12A, 12B:
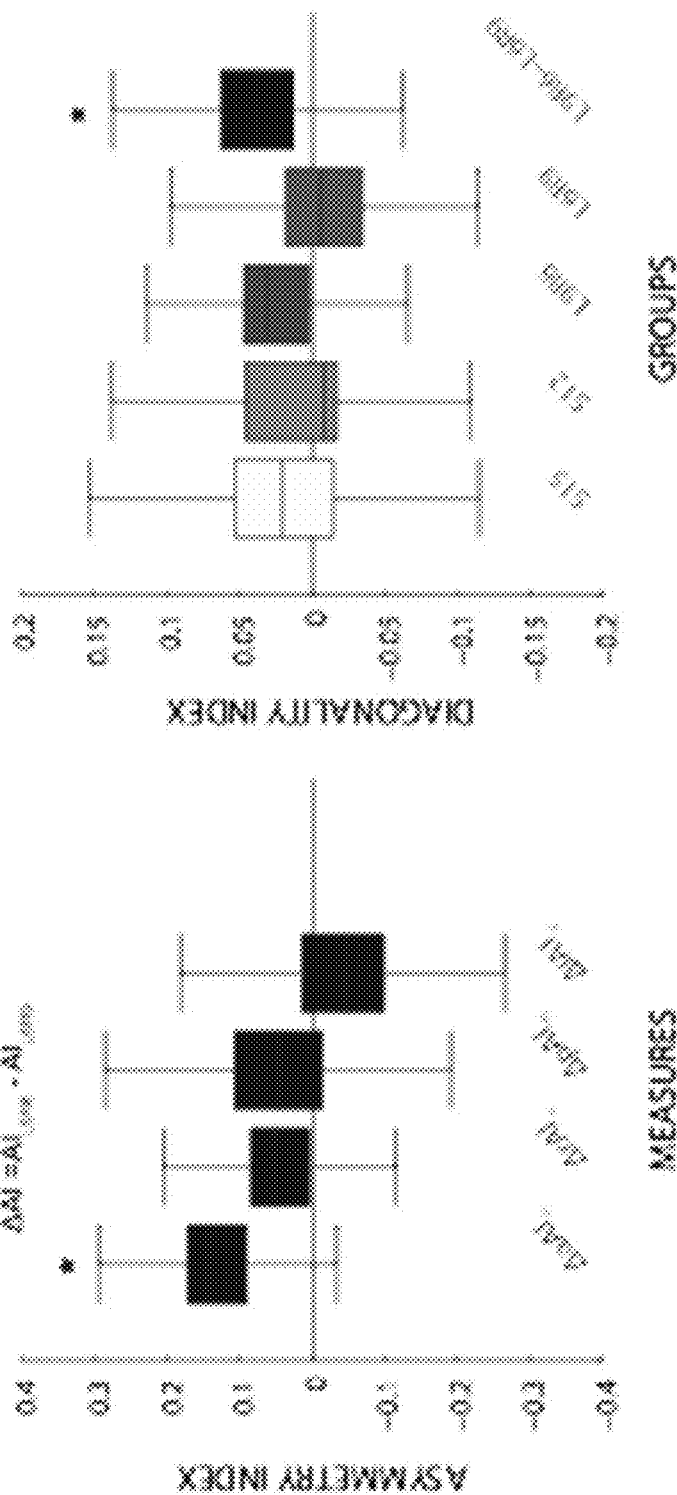
FIGS. 12A-12B show an absolute difference in asymmetric indices (AI), and an analysis of distribution of diagonality indices (DI), respectively.

Referring to FIGS. 12A-12B, FIG. 12A shows absolute difference in asymmetric indices (AI) between conditions L9R6 and L6R9 that were tested with one-way ANOVA with post-hoc t-test analysis adjusted with the Bonferroni correction for multiple tests. The change in forelimb asymmetry ($\Delta aAI_h$) between L9R6 and L6R9 was significant. FIG. 12B shows an analysis of distribution of diagonality indices (DI) of conditions S15, S12, L9R6 and L6R9 using one-way ANOVA with the post-hoc t-test of the difference between asymmetric tasks (black).

As this method can be made to rely on the animals' natural ability to solve the asymmetric foot placement, some animals may exhibit gallop-like behavior where the posterior limbs were simultaneously in swing. This gait was observed in three animals, and the behavior was excluded from further analyses.

The presently disclosed device and method sets forth a behavioral task that can quantitatively assess changes in precise control of asymmetric locomotor behaviors. The existence of the spinal CPG has been functionally demonstrated for some time[20], but the anatomical and functional characteristics that describe its mechanism as well as its modulatory inputs from descending or sensory feedback pathways have not been characterized until the past decade[6,21,22]. The current consensus is that the intrinsic spinal, sensory feedback, and descending commands are tightly integrated in the generation of locomotor behavior.[1]

The asymmetric precise foot placement task presented herein can be further designed to functionally challenge the control systems responsible for the dexterous asymmetric control of stepping known to require cortical inputs.[23,24] This performance can be assessed relative to the symmetric tasks that are less reliant on the descending cortical and brainstem control. Thus, the device and method can enable discerning the contributions of the spinal and descending pathways. Since the motor cortex is directly involved in the modulation of muscle phases during locomotion, reaching, and postural adjustments[9,10,25], the analysis of phase modulation in response to imposed asymmetric precise stepping tasks may provide a basis for describing changes in volitional control. This can be evident in the significant lateralized phase modulation between left- and right-favored tasks, characterized by the differences in asymmetry indices. The inventors have also observed changes in whole body coordination that required diagonal coupling between contralateral forelimbs and hind-limbs, characterized by differences in the diagonal index.

Both focal stroke[26,27] and spinal cord hemilesion[28,29] animal models can cause mild to moderate movement deficits akin to those observed clinically. With existing animal models, cortical lesioning of the corticospinal tract impedes or prevents precise stepping.[30,31] The application of our methodology to the characterization of cortical impairment in stroke models is yet to be described, though some of our preliminary data on rats with middle cerebral artery occlusions showed increased AI, and even a negative slope of the stance phase with increasing cycle duration for the limb on the side contralateral to stroke. This may correspond to a delay in the onset of consecutive locomotor phases, which is consistent with an asymmetry in both the step length ratio and the single limb support time observed in post-stroke patients.[15,32]

A limitation of this method may be that it may be inappropriate for the analysis of severely affected animals. However, this subgroup is not necessarily the focus of attention in studies of hemiparetic animals. Furthermore, subjective tracking of this type of deficit may require additional sub scales that may also be associated with high inter-rater variability, creating demand for gross computational methodology[33]. Thus, the challenge remains not in the assessment of deficits in the severely affected animals, but in the assessment of the mild to severe subgroup. Moreover, the ability to distinguish damage to specific hierarchical areas has been virtually impossible in a non-invasive method. Thus, the devices and methods of use disclosed herein can be an effective tool for the evaluation of moderate impairment by monitoring modulatory activity of the motor antagonistic phases that drive the CPG with different speed demands, presumably contributed by higher order factors of the motor control hierarchy.[6]

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. While certain dimensions for elements have been disclosed here, such dimensions are exemplary only and other dimensions, both smaller and larger, are contemplated herein without departing from the spirit and scope of the invention. Additionally, the disclosure of a range of values is a disclosure of every numerical value within that range, including the end points.

REFERENCES

1. Curzon, P., Zhang, M., Radek, R. J. & Fox, G. B. The Behavioral Assessment of Sensorimotor Processes in the Mouse: Acoustic Startle, Sensory Gating, Locomotor Activity, Rotarod, and Beam Walking. at <http://www.ncbi.nlm.nih.gov/books/NBK5236/> (2009).
2. Basso, D. M., Beattie, M. S. & Bresnahan, J. C. A sensitive and reliable locomotor rating scale for open field testing in rats. *Journal of Neurotrauma* 12 (1), 1-21 at <http://www.ncbi.nlm.nih.gov/pubmed/7783230> (1995).
3. Basso, D. M., Beattie, M. S. & Bresnahan, J. C. Graded histological and locomotor outcomes after spinal cord contusion using the NYU weight-drop device versus transection. *Experimental Neurology* 139 (2), 244-56, doi:10.1006/exnr.1996.0098 (1996).
4. Li, S., Shi, Z., et al. Assessing gait impairment after permanent middle cerebral artery occlusion in rats using an automated computer-aided control system. *Behavioural Brain Research* 250, 174-91, doi:10.1016/j.bbr.2013.04.044 (2013).
5. Vandeputte, C., Taymans, J.-M., et al. Automated quantitative gait analysis in animal models of movement disorders. *BMC Neuroscience* 11, 92, doi:10.1186/1471-2202-11-92 (2010).
6. Yakovenko, S. *Chapter 10—A hierarchical perspective on rhythm generation for locomotor control. Progress in Brain Research* 188, doi:10.1016/B978-0-444-53825-3.00015-2 (Elsevier BV.: 2011).
7. Giszter, S. F., Hockensmith, G., Ramakrishnan, A. & Udoekwere, U. I. How spinalized rats can walk: biomechanics, cortex and hindlimb muscle scaling—implications for rehabilitation. *Annals of the New York Academy of Sciences* 1198, 279-293, doi:10.1111/j.1749-6632.2010.05534.x.How (2010).
8. Smith, J. L., Edgerton, V. R., Eldred, E. & Zernicke, R. F. The chronic spinalized cat: a model for neuromuscular plasticity. *Birth Defects Original Article Series* 19 (4), 357-73 at <http://www.ncbi.nlm.nih.gov/pubmed/6871404> (1983).
9. Yakovenko, S. & Drew, T. A motor cortical contribution to the anticipatory postural adjustments that precede reaching in the cat. *Journal of Neurophysiology* 102 (2), 853-74, doi:10.1152/jn.00042.2009 (2009).
10. Yakovenko, S., Krouchev, N. & Drew, T. Sequential Activation of Motor Cortical Neurons Contributes to Intralimb Coordination During Reaching in the Cat by Modulating Muscle Synergies. *Journal of Neurophysiology* 105, 388-409, doi:10.1152/jn.00469.2010. (2011).

11. Pizzi, A., Carlucci, G., Falsini, C., Lunghi, F., Verdesca, S. & Grippo, A. Gait in hemiplegia: Evaluation of clinical features with the Wisconsin Gait Scale. *Journal of Rehabilitation Medicine* 39 (9), 170-174, doi:10.2340/16501977-0026 (2007).

12. Bohannon, R. W., Horton, M. G. & Wikholm, J. B. Importance of four variables of walking to patients with stroke. *International Journal of Rehabilitation Research* 14 (3), 246-50 at <http://www.ncbi.nlm.nih.gov/pubmed/1938039> (1991).

13. Richards, C., Malouin, F., Dumas, F. & Tardif, D. Gait velocity as an outcome measure of locomotor recovery after stroke. *Gait Analysis. Theory and Application*, 355-364 (1995).

14. Thaut, M. H., McIntosh, G. C. & Rice, R. R. Rhythmic facilitation of gait training in hemiparetic stroke rehabilitation. *Journal of the Neurological Sciences* 151, 207-212, doi:10.1016/S0022-510X(97)00146-9 (1997).

15. Hsu, A.-L., Tang, P.-F. & Jan, M.-H. Analysis of impairments influencing gait velocity and asymmetry of hemiplegic patients after mild to moderate stroke. *Archives of Physical Medicine and Rehabilitation* 84 (8), 1185-1193, doi:10.1016/S0003-9993(03)00030-3 (2003).

16. Jansen, K., De Groote, F., Duysens, J. & Jonkers, I. Muscle contributions to center of mass acceleration adapt to asymmetric walking in healthy subjects. *Gait & Posture* 38 (4), 739-44, doi:10.1016/j.gaitpost.2013.03.013 (2013).

17. Halbertsma, J. M. The stride cycle of the cat: the modelling of locomotion by computerized analysis of automatic recordings. *Acta physiologica Scandinavica* 521, 1-75 at <http://www.ncbi.nlm.nih.gov/pubmed/6582764> (1983).

18. Metz, G. a & Whishaw, I. Q. The ladder rung walking task: a scoring system and its practical application. *Journal of Visualized Experiments: JoVE* (28), 4-7, doi:10.3791/1204 (2009).

19. Hogg, R. V & Ledolter, J. *Engineering Statistics*. (MacMillan: New York, N.Y., 1987).

20. Brown, T. G. The intrinsic factors in the act of progression in the mammal. *Proceedings of the Royal Society of London. Series B, Containing Papers of a Biological Character* 84 (572), 308-319 (1911).

21. Kiehn, O. Locomotor circuits in the mammalian spinal cord. *Annual Review of Neuroscience* 29, 279-306, doi:10.1146/annurev.neuro.29.051605.112910 (2006).

22. Blitz, D. M. & Nusbaum, M. P. State-dependent presynaptic inhibition regulates central pattern generator feedback to descending inputs. *The Journal of Neuroscience* 28 (38), 9564-74, doi:10.1523/JNEUROSCI.3011-08.2008 (2008).

23. Martin, J. H. & Ghez, C. Red nucleus and motor cortex: parallel motor systems for the initiation and control of skilled movement. *Behavioural Brain Research* 28 (1-2), 217-23 at <http://www.ncbi.nlm.nih.gov/pubmed/3382515>

24. Drew, T., Jiang, W., Kably, B. & Lavoie, S. Role of the motor cortex in the control of visually triggered gait modifications. *Canadian Journal of Physiology and Pharmacology* 74 (4), 426-42 at <http://www.ncbi.nlm.nih.gov/pubmed/8828889> (1996).

25. Drew, T., Andujar, J.-E., Lajoie, K. & Yakovenko, S. Cortical mechanisms involved in visuomotor coordination during precision walking. *Brain Research Reviews* 57 (1), 199-211, doi:10.1016/j.brainresrev.2007.07.017 (2008).

26. Longa, E. Z., Weinstein, P. R., Carlson, S. & Cummins, R. Reversible middle cerebral artery occlusion without craniectomy in rats. *Stroke* 20 (1), 84-91, doi:10.1161/01.STR.20.1.84 (1989).

27. Uluç, K., Miranpuri, A., Kujoth, G. C., Aktüre, E. & Başkaya, M. K. Focal Cerebral Ischemia Model by Endovascular Suture Occlusion of the Middle Cerebral Artery in the Rat. *Journal of Visualized Experiments: JoVE* 48 (e1978), 1-5, doi:10.3791/1978 (2011).

28. Hackney, D. B., Finkelstein, S. D., Hand, C. M., Markowitz, R. S. & Black, P. Postmortem Magnetic Resonance Imaging of Experimental Spinal Cord Injury: Magnetic Resonance Findings versus In Vivo Functional Deficit. *Neurosurgery* 35 (6), 1104-1111 (1994).

29. Kjaerulff, O. & Kiehn, O. Distribution of Networks Generating and Coordinating Locomotor Activity in the Neonatal Rat Spinal Cord In Vitro: A Lesion Study. *The Journal of Neuroscience* 16 (18), 5777-5794 (1996).

30. Liddell, E. G. T. & Phillips, C. G. Striatal and pyramidal lesions in the cat. *Brain* 69 (4), 264-279, doi:10.1093/brain/69.4.264 (1946).

31. Beloozerova, I. N. & Sirota, M. G. The Role of the Motor Cortex in the Control of Accuracy of Locomotor Movements in the Cat. *Journal of Physiology* 461, 1-25 (1993).

32. Hill, K. D., Goldie, P. A., Baker, P. A. & Greenwood, K. M. Retest reliability of the temporal and distance characteristics of hemiplegic gait using a footswitch system. *Archives of Physical Medicine and Rehabilitation* 75 (5), 577-83 at <http://www.ncbi.nlm.nih.gov/pubmed/8185453> (1994).

33. Hillyer, J. E. & Joynes, R. L. A new measure of hindlimb stepping ability in neonatally spinalized rats. *Behavioural Brain Research* 202 (2), 291-302, doi:10.1016/j.bbr.2009.04.009 (2009).

What is claimed is:

1. A method for quantitatively assessing the changes in control of asymmetric locomotor behavior of an animal comprising analyzing the phase modulation in response to one or more of an imposed asymmetric stepping task wherein either a right inter-stride length, or a left inter-stride length, or a combination of said right inter-stride length and said left inter-stride length of said animal, are adjusted in relation to stride-length for quantitatively assessing changes in control of asymmetric locomotor behavior.

2. A method for quantitatively assessing the changes in control of asymmetric locomotor behavior of an animal comprising analyzing the phase modulation in response to one or more of an imposed asymmetric stepping task for quantitatively assessing changes in control of asymmetric locomotor behavior, and observing changes in whole body coordination of said animal requiring diagonal coupling between contralateral forelimbs and hind-limbs of said animal characterized by differences in diagonal angle.

3. The method of claim 2, further comprising providing an animal having either a focal stroke or spinal cord hemilesion.

4. A walkway gait device comprising an elevated grid or framework having at least one platform having a face and at least two or more pegs located in front or back of said platform, each peg having a face and at least one side that extends vertically from said face, said face of said peg positioned in proximity to said face of said platform, including wherein each peg has a pressure sensor or switch, wherein one or more of said pressure sensors or switches are in communication with a detection unit for capturing the pressure detected by one or more of said pressure sensors or switches.

5. The walkway gait device of claim 4, including wherein one or more said pegs may be adjusted in one or more of a horizontal, a lateral, or a vertical direction relative to said face of said platform.

6. The walkway gait device of claim 4, including said platform and at least two pegs located in succession of each other relative to said platform, and a second platform located in juxtaposition to a peg that is located farthest from said platform such that the pegs are located and spaced between said platform and said second platform.

7. The walkway gait device of claim 6, including wherein one or more said pegs may be adjusted in one or more of a horizontal, a lateral, or a vertical direction relative to said face of said platform and said face of said second platform.

8. The walkway gait device of claim 4, wherein said grid contains at least three platforms each having its own face and wherein each platform is separated from each other by at least two of said pegs, such that said three or more platforms form a closed loop path.

9. The walkway gait device of claim 8, including wherein one or more said pegs may be adjusted in one or more of a horizontal, a lateral, or a vertical direction relative to said face of said platform.

10. The walkway device of claim 8 wherein said closed path loop comprises one or more conditions to evaluate locomotion performance, impose step restrictions, and/or track corticospinal function.

11. The walkway device of claim 4, wherein the face of at least one of said pegs may be tilted up or down relative to the face of another peg or to the face of at least one or more of said platforms.

12. The walkway gait device of claim 4, including an imaging device that is capable of capturing images of said framework.

13. The walkway gait device of claim 12, wherein said imaging device is in communication with a computational apparatus for analyzing one or more images captured by said imaging device.

14. The walkway gait device of claim 12, wherein said imaging device is a camera that is pointed at said framework.

15. The walkway gait device of claim 14, wherein said camera is a video camera.

16. A device for quantitative analysis of gait, comprising:
a support framework structured to support a plurality of pegs, the plurality of pegs forming a walkway to accommodate an animal walking along the plurality of pegs, the walkway comprising a first distal end and a second distal end;
a rest platform located at each of the first distal end and the second distal end;
at least one sidewall affixed to the support framework adjacent the walkway;
a path defined by the walkway and the at least one sidewall, the path comprising a central pathway running along its center from the first distal end to the second distal end forming a path first side and a path second side; and
at least one sensor and at least one detection unit associated with at least one peg, the at least one sensor generating a signal when a foot by the animal is placed on the at least one peg and transmitting the signal to the detection unit, the detection unit detecting placement of the foot by the animal on the at least one peg;
wherein each peg comprises a platform section upon which the animal places the foot when walking along the path;
wherein the plurality of pegs is arranged in a linear array along the path and each peg is arranged in a staggered manner so that the platform section of each adjacent peg in the linear array is located on an opposite side of the central pathway;
wherein a distance between each adjacent platform section is (d) and a distance between each consecutive platform section of a same side of the central pathway is a stride-length (SL); and
wherein placement of each peg relative to other pegs and relative to the support framework is adjustable.

17. A device for quantitative analysis of gait, comprising:
a support framework configured as a square structure to support a plurality of pegs, the support framework comprising a first side-length, a second side-length, a third side-length, and a fourth side-length, the plurality of pegs forming a walkway along each side-length to accommodate an animal walking along the plurality of pegs, each walkway comprising a distal end located at each corner of the support framework;
a rest platform located at each corner;
at least one sidewall affixed to the support framework adjacent each walkway;
a path defined by each walkway and the at least one sidewall adjacent thereto, the path comprising a central pathway running along its center from the distal ends of each walkway forming a path first side and a path second side; and
at least one sensor and at least one detection unit associated with at least one peg within each walkway, the at least one sensor generating a signal when a foot by the animal is placed on the at least one peg and transmitting the signal to the detection unit, the detection unit detecting placement of the foot by the animal on the at least one peg;
wherein each peg comprises a platform section upon which the animal places the foot when walking along the path;
wherein the plurality of pegs is arranged in a linear array along the path and each peg is arranged in a staggered manner so that the platform section of each adjacent peg in the linear array is located on an opposite side of the central pathway;
wherein a distance between each adjacent platform section is (d) and a distance between each consecutive platform section of a same side of the central pathway is a stride-length (SL);
wherein placement of each peg relative to other pegs and relative to the support framework is adjustable; and
wherein the (d) and the (SL) on an individual path are at least two parameters that define a condition.

18. The device of claim 17 wherein:
the condition for the path of the first side-length is different from the condition for the path of the second side-length, the condition for the path of the third side-length, and the condition for the path of the fourth side-length;
the condition for the path of the second side-length is different from the condition for the path of the first side-length, the condition for the path of the third side-length, and the condition for the path of the fourth side-length;

the condition for the path of the third side-length is different from the condition for the path of the first side-length, the condition for the path of the second side-length, and the condition for the path of the fourth side-length; and the condition for the path of the fourth side-length is different from the condition for the path of the first side-length, the condition for the path of the second side-length, and the condition for the path of the third side-length.

19. The device of claim 17, wherein the condition is a set of parameters to evaluate locomotion performance, impose step restrictions, and/or track corticospinal function.

20. A method for quantitative analysis of gait, comprising:
constructing a device, generating at least one path along which an animal is forced to walk during at least one walking campaign;
adjusting at least one condition parameter to generate at least one condition, wherein each condition parameter is associated with the at least one path and each condition comprises devising a set of condition parameters to cause the animal to perform at least one of a symmetric locomotor task and an asymmetric locomotor task when the animal is forced to perform the at least one walking campaign;
training the animal on the device by at least acclimating the animal to the at least one condition by causing the animal to perform the at least one walking campaign and/or at least one session of the at least one walking campaign;
performing the at least one acclimation walking campaign and/or acclimation session until at least one of appropriate or desired inter-stride lengths are achieved for each condition and locomotor standards for each condition are met;
causing the animal to perform the at least one walking campaign on the device after the training, wherein each of the at least one walking campaigns is derived by generating randomized walking sessions; and
recording data obtained from the at least one walking campaign and performing data analysis of the data.

21. The method of claim 20, wherein constructing the device further comprises generating a support framework configured as a square structure to support a plurality of pegs, the support framework comprising a first side-length having a first path, a second side-length having a second path, a third side-length having a third path, and a fourth side-length having a fourth path.

22. The method of claim 20, wherein generating the at least one condition further comprises:
generating first condition so that when the animal is forced to perform the at least one walking campaign, the animal performs a symmetric locomotor task;
generating a second condition so that when the animal is forced to perform the at least one walking campaign, the animal performs a modified symmetric locomotor task;
generating a third condition so that when the animal is forced to perform the at least one walking campaign, the animal performs a left-side asymmetric locomotor task; and
generating a fourth condition so that when the animal is forced to perform the at least one walking campaign, the animal performs a right-side asymmetric locomotor task.

23. The method of claim 20, wherein generating the locomotor standards for the at least one condition comprises ensuring the animal is walking rather than exhibiting other gaiting behavior.

24. The method of claim 20, wherein the animal is a rat and the locomotive standards for the at least one condition comprise:
consistent walking without stops or missteps;
minimal head-bobbing exhibited by the rat;
a back of the rat is arched and a tail of the rat is raised during locomotion; and
each limb of the rat is clearly visible from an orthogonal view of the path at an onset and an offset of a stance phase.

25. A walkway gait device comprising an elevated grid or framework having at least one platform having a face and at least two or more pegs located in front or back of said platform, each peg having a face and at least one side that extends vertically from said face, said face of said peg positioned in proximity to said face of said platform.

26. The walkway gait device of claim 25, including an imaging device that is capable of capturing images of said framework.

27. The walkway gait device of claim 26, wherein said imaging device is in communication with a computational apparatus for analyzing one or more images captured by said imaging device.

28. The walkway gait device of claim 26, wherein said imaging device is a camera that is pointed at said framework.

29. The walkway gait device of claim 28, wherein said camera is a video camera.

30. The walkway gait device of claim 25, including wherein one or more said pegs may be adjusted in one or more of a horizontal, a lateral, or a vertical direction relative to said face of said platform.

31. The walkway gait device of claim 25, including said platform and at least two pegs located in succession of each other relative to said platform, and a second platform located in juxtaposition to a peg that is located farthest from said platform such that the pegs are located and spaced between said platform and said second platform.

32. The walkway gait device of claim 31, including wherein one or more said pegs may be adjusted in one or more of a horizontal, a lateral, or a vertical direction relative to said face of said platform and said face of said second platform.

33. The walkway gait device of claim 25, wherein said grid contains at least three platforms each having its own face and wherein each platform is separated from each other by at least two of said pegs, such that said three or more platforms form a closed loop path.

34. The walkway gait device of claim 33, including an imaging device that is capable of capturing images of said framework.

35. The walkway gait device of claim 33, wherein said closed path loop comprises one or more conditions to evaluate locomotion performance, impose step restrictions, and/or track corticospinal function.

36. The walkway gait device of claim 33 including wherein one or more said pegs may be adjusted in one or more of a horizontal, a lateral, or a vertical direction relative to said face of said platform.

37. The walkway gait device of claim 25, wherein the face of at least one of said pegs may be tilted up or down relative to the face of another peg or to the face of at least one or more of said platforms.

* * * * *